United States Patent
Zhao et al.

(10) Patent No.: US 10,555,901 B2
(45) Date of Patent: *Feb. 11, 2020

(54) LIQUISOFT CAPSULES

(71) Applicant: PATHEON SOFTGELS INC, High Point, NC (US)

(72) Inventors: YinYan Zhao, Greensboro, NC (US); Yunhua Hu, Cary, NC (US); Mervin Williams, Jr., Jamestown, NC (US); Tatyana Dyakonov, Greensboro, NC (US); Saujanya Gosangari, Jamestown, NC (US); Chue Yang, Greensboro, NC (US); Henricus Marinus Gerardus Maria Van Duijnhoven, den Bosch (NL); Martin Piest, Tilburg (NL); Aqeel A Fatmi, High Point, NC (US)

(73) Assignee: PATHEON SOFTGELS INC, High Point, NC (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/795,814

(22) Filed: Oct. 27, 2017

(65) Prior Publication Data

US 2018/0049979 A1    Feb. 22, 2018

Related U.S. Application Data

(63) Continuation of application No. 15/080,614, filed on Mar. 25, 2016, now Pat. No. 9,867,779.

(60) Provisional application No. 62/236,297, filed on Oct. 2, 2015, provisional application No. 62/138,468, filed on Mar. 26, 2015.

(51) Int. Cl.
| | |
|---|---|
| *A61K 9/00* | (2006.01) |
| *A61K 31/485* | (2006.01) |
| *A61K 9/48* | (2006.01) |
| *A61K 31/045* | (2006.01) |

(52) U.S. Cl.
CPC .......... *A61K 9/0056* (2013.01); *A61K 9/4825* (2013.01); *A61K 9/4858* (2013.01); *A61K 9/4866* (2013.01); *A61K 31/045* (2013.01); *A61K 31/485* (2013.01)

(58) Field of Classification Search
CPC .................................................. A61K 9/4825
See application file for complete search history.

(56) References Cited

U.S. PATENT DOCUMENTS

| | | |
|---|---|---|
| 3,760,035 A | 9/1973 | Kelley |
| 4,301,178 A | 11/1981 | Mackay |
| 4,386,106 A | 5/1983 | Keller |
| 4,515,769 A | 5/1985 | Keller |
| 4,935,243 A | 6/1990 | Berry |
| 6,258,380 B1 | 7/2001 | Overholt |
| 7,723,390 B2 | 5/2010 | Garavani |
| 8,097,279 B2 | 1/2012 | Kindt |
| 8,241,665 B2 | 8/2012 | Kindt |
| 8,414,916 B2 | 4/2013 | Kindt |
| 8,765,174 B2 | 7/2014 | Kindt |
| 9,072,677 B2 | 7/2015 | Kindt |
| 9,668,976 B2 | 6/2017 | Kindt |
| 2007/0172523 A1 | 7/2007 | Hirata |
| 2014/0073698 A1* | 3/2014 | Badabhagni ......... A61K 9/4866 514/570 |

FOREIGN PATENT DOCUMENTS

| | | |
|---|---|---|
| FR | 2535608 A1 | 5/1984 |
| WO | 2000051574 | 9/2000 |

* cited by examiner

*Primary Examiner* — Kyle A Purdy
(74) *Attorney, Agent, or Firm* — Michael Best & Friedrich LLP

(57) ABSTRACT

Described herein are oral pharmaceutical compositions suitable for chewing, sucking, or buccal dissolution comprising soft gel capsules and liquid fills, methods for making the same, and methods for treating subjects in need thereof with such capsules. In particular, oral pharmaceutical compositions comprising chewable, suckable, or dissolvable soft gel capsules with various flowable fill compositions are described.

16 Claims, 1 Drawing Sheet

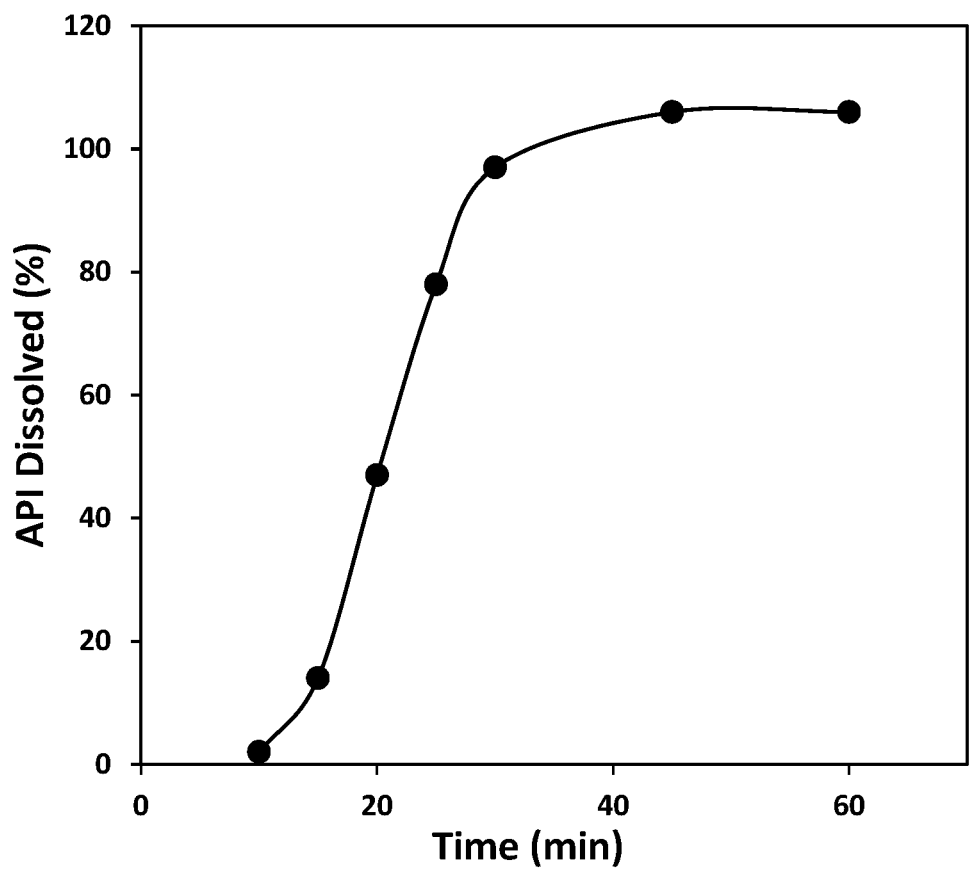

LIQUISOFT CAPSULES

CROSS REFERENCE TO RELATED APPLICATIONS

This application is a continuation of U.S. patent application Ser. No. 15/080,614, filed on Mar. 25, 2016, which claims priority to U.S. Provisional Patent Application Nos. 62/138,468, filed on Mar. 26, 2015, and 62/236,297, filed on Oct. 2, 2015, each of which is incorporated herein in its entirety by express reference thereto.

TECHNICAL FIELD

Described herein are oral pharmaceutical compositions suitable for chewing, sucking, or buccal dissolution comprising soft gel capsules and liquid fills, methods for making the same, and methods for treating subjects in need thereof with such capsules. In particular, oral pharmaceutical compositions comprising chewable, suckable, or dissolvable soft gel capsules with various flowable fill compositions are described.

BACKGROUND

Chewable dosage forms are typically manufactured as solids, such as chewable tablets, or elastic semi-solids such as chewing gums, molded gels, or chewable soft gelatin capsules. While elastic semi-solid forms provide better mouth feel and customer acceptance, chewable soft gelatin capsules (e.g., "soft gels") have a benefit of being ingestible and can deliver accurate amounts of active ingredients to the oral cavity and digestive system.

Soft gels have gained popularity and acceptance due to their elegant and clear gelatin shells. Furthermore, soft gel capsules are uniform, stable, dissolve quickly, allow for liquid formulations, and are easier for most subjects to swallow.

Soft gel capsules are typically formed of a capsule shell encapsulating a liquid matrix fill. Several types of soft gel capsules can be chewed by the user. See e.g., U.S. Pat. Nos. 6,258,380; 8,097,279; 8,241,665; 8,414,916; and 8,765,174. Such chewable soft capsules are chewed by the subject to release the fill contents into the mouth, instead of swallowing the capsule with the fill still encapsulated within the shell. Often the fill of chewable soft capsules contains substantial amounts of gelatin giving the fill a semi-solid characteristic, rather than a true liquid character.

Although chewable soft capsules provide an effective dosage system, user acceptance has been limited by the organoleptic properties of the capsules, which are sometimes criticized as being leathery or rubbery. Chewable soft capsules sometimes have a distinguishable difference between the shell and fill in terms of texture and mouth-feel. Some users experience difficulty consuming the masticated sheath after the internal fill has been released. In addition, chewable soft capsules tend to harden over time.

Thus, there is an unmet need for chewable soft capsule dosage forms comprising liquid fills, where the capsule shell can be chewed, sucked, or that dissolves in the mouth and releases the active ingredient in a liquid form in the oral cavity. Accordingly, it is desirable to develop chewable soft gelatin capsules having desirable organoleptic properties that can be sucked or that slowly dissolve in the mouth to release pleasant-tasting or refreshing liquid fills.

SUMMARY

One embodiment described herein is an oral pharmaceutical composition suitable for chewing, sucking, or buccal dissolution comprising a soft capsule with a flowable fill comprising one or more active pharmaceutical ingredients, nutraceuticals, flavors, or refresheners. Exemplary embodiments are cough and cold over-the-counter (OTC) remedies; nonsteroidal anti-inflammatory drugs (NSAIDs) for treating pain; nicotine satiation, nicotine-replacement therapy, or smoking cessation therapy; breath fresheners or treatments for halitosis; treatments for temporary discomforts of the stomach and gastrointestinal tract; or as a delivery means for any of the active pharmaceuticals described herein.

Another embodiment described herein is an oral pharmaceutical composition suitable for chewing, sucking, or buccal dissolution comprising a shell encapsulating a matrix, the shell comprising: (a) one or more film-forming polymers; (b) one or more plasticizers; (c) one or more polymer modifiers; (d) one or more first sweeteners; (e) one or more first solvents; (f) optionally, one or more excipients; and a matrix comprising: (g) one or more hydrophilic vehicles; (h) one or more flavors; (i) one or more second sweeteners; (j) one or more second solvents; (k) one or more active pharmaceutical ingredients; and (l) optionally, one or more excipients. In one aspect describe herein, the film-forming polymer comprises one or more of gelatin, partially hydrolyzed gelatin, hydrolyzed gelatin, hydrolyzed collagen, or combinations thereof. In another aspect describe herein, the plasticizer comprises one or more of glycerol, maltitol, mannitol, xylitol, lycasin, or combinations thereof. In another aspect describe herein, the polymer modifier comprises one or more of citric acid, acetic acid, lactic acid, malic acid, tartaric acid, or combinations thereof. In another aspect describe herein, the hydrophilic vehicle comprises propylene glycol, polyethylene glycol 400, polyvinylpyrrolidone K30, glycerin, sorbitol, xylitol, maltitol, or combinations thereof. In another aspect describe herein, the first sweetener comprises sucralose, aspartame, stevia, acesulfame potassium, xylitol, or combinations thereof. In another aspect describe herein, the flavoring comprises citric acid, lactic acid, sodium citrate, orange flavor, eucalyptol, peppermint oil, methyl salicylate, glycine, or combinations thereof. In another aspect describe herein, the second sweetener comprises mannitol, maltitol, xylitol, thaumatin, glycyrrhizic acid salts, acesulfame potassium, acesulfame salts, sucralose, aspartame, stevia, or combinations thereof. In another aspect describe herein, the active pharmaceutical ingredient comprises one or more of: astemizole, azelastine, azatadine, brompheniramine, carbinoxamine, cetirizine, chlorpheniramine, clemastine, cyproheptadine, desloratadine, dexbrompheniramine, dexchlorpheniramine, diphenhydramine, fexofenadine, hydroxyzine, levocetirizine, loratadine, phenindamine, pheniramine, phenyltoloxamine, promethazine, pyrilamine, terfenadine, tripelennamine, triprolidine, acetyl dihydrocodeine, benproperine, benzonatate, benzylmorphine, bibenzonium bromide, butamirate, butorphanol, carbetapentane, chlophedianol, clobutinol, clofedanol, cloperastine, codeine, dextromethorphan, dextromethorphan hydrobromide, diacetylmorphine, dibunate, dihydrocodeine, dimemorfan, dimethoxanate, diphenhydramine, dropropizine, droxypropine, ethylmorphine, fedrilate, glaucine, hydrocodone, hydromorphone, isoaminile, laudanum, levodropropizine, levomethadone, levopropoxyphene, meprotixol, methadone, morclofone, nepinalone, nicocodine, nicodicodine, normethadone, noscapine, oxeladin, oxolamine, pentoxyverine, pholcodine, pipazetate, piperidione, prenoxdiazine, tipepidine, zipeprol, acetylcysteine, althea root, ambroxol, antimony pentasulfide, bromhexine, carbocisteine, cineole, combinations, combinations, creosote, dembrexine hydrochloride, domiodol, dornase alfa, eprazinone, erdosteine, guaiacolsulfonate, guaifenesin, hederae helicis folium, ipecacuanha, letosteine, levo verbenone, mannitol, mesna, neltenexine, potassium iodide, senega, sobrerol, stepronin, tiopronin, tyloxapol, pseudoephedrine, cetirizine, loratadine, fexofenadine, diphenhydramine, levocetirizine, desloratadine, phenol, ethanol, thymol, eucalyptol, ethanol, methyl salicylate, chlorhexidine gluconate, cetylpyridinium chloride, hexetidine, triclosan, hydrogen peroxide, domiphen bromide, bismuth subsalicylate, loperamide hydrochloride, aluminum hydroxide, magnesium hydroxide, magnesium aluminum silicate simethicone, aluminum carbonate, calcium carbonate, sodium bicarbonate, hydrotalcite, magaldrate, cimetidine, famotidine, nizatidine, ranitidine, lansoprazole, omeprazole, esomeprazole, rabeprazole, pantoprazole, dexlansoprazole, diphenoxylate, dicyclomine, loperamide, rifaximin, alosetron, cholestyramine, linaclotide, lubiprostone, methylcellulose, polycarbophil, psyllium, mineral oil, glycerol, docusate sodium, sodium bicarbonate, sodium phosphate, magnesium citrate, magnesium oxide, magnesium sulfate, bisacodyl, sennosides, senna, castor oil, alclometasone, amcinonide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fluprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol, 5-fluorouracil, 5-fluorodeoxyuridine, capecitabine, calcium supplements, calcimimetics, cinacalcet, nicotine, nicotine polacrilex, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides, ganglioside derivatives, tirilazad, riluzole, xaliproden, hydroxybutyric acid, amifampridine, doxylamine, diphenhydramine hydrochloride, melatonin, 1-theanine, monofluorophosphate, lactoferrin, lysozyme, lactoperoxidase, glucose oxidase, mutanase, dextranase, glycerol, carbamide peroxide, sodium bicarbonate, hydrated silica, silicon dioxide, polyvinylpyrrolidone, potassium nitrate, sodium monofluorophosphate, sodium tripolyphosphate, strontium chloride, potassium nitrate, strontium acetate, strontium chloride, calcium sodium phosphosilicate, benzocaine, lidocaine, clove oil, sodium bicarbonate, citric acid, tartaric acid, aspirin, ibuprofen, aceclofenac, acemetacin, aloxiprin, azapropazone, benorilate, bromfenac, carprofen, celecoxib, choline magnesium salicylate, diclofenac, diflunisal, etodolac, etoricoxib, fisalamine, fenbufen, fenoprofen, flurbiprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, paracetamol, oxyphenbutazone, parecoxib, phenylbutazone, piroxicam, salicyl salicylate, sulindac, sulfinpyrazone, suprofen, tenoxicam, tiaprofenic acid, tolmetin, valdecoxib, acetylsalicylic acid, aloxiprin, aminophenazone, anilides, benorilate, benzomorphan derivatives, bezitramide, bucetin, buprenorphine, butorphanol, carbasalate calcium, choline salicylate, codeine, dextromoramide, dextropropoxyphene, dezocine, diamorphine, diflunisal, dihydrocodeine, dihydrocodone, dihydromorphine, diphenylpropylamine derivatives, dipyrocetyl, ethenzamide, fentanyl, floctafenine, flupirtine, glafenine, guacetisal, hydrocodone, hydrocodone bitartrate, hydromorphone, hydromorphone hydrochloride, imidazole salicylate, ketobemidone, metamizole sodium, methadone, morphinan derivatives, morphine, morphine sulphate pentahydrate, morphine-6-glucuronode, morpholine salicylate, nalbuphine, natural opium alkaloids, nefopam, nicomorphine, nifenazone, non-steroidal anti-inflammatory drugs (NSAID), norhydrocodone, noroxycodone, opioids, opium, oripavine derivatives, oxycodeine, oxycodone, oxycodone hydrochloride, oxymorphone, papaveretum, pentazocine, pethidine, phenacetin, phenazocine, phenazone, phenylpiperidine derivatives, piritramide, potassium salicylate, propacetamol, propyphenazone, pyrazolones, rimazolium, salicylamide, salicylic acid derivatives, salsalate, sodium salicylate, tapentadol, tilidine, tramadol, viminol, ziconotide, caffeine, taurine, ginko biloba, glucuronolactone, inositol, niacin, niacinamide, D-pantothenol, panax ginseng root extract, pyridoxine HCl, vitamin B12, cyanocobalamin, riboflavin, guarana, L-carnitine, vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, para-aminobenzoic acid, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfinates, phytosterols, anthraquinones, capsaicin, piperine, chlorophyll, betaine, oxalic acid, acetyl-L-carnitine, allantoin, androstenediol, androstendione, betaine (trimethylglycine), caffeine, calcium pyruvate (pyruvic acid), carnitine, carnosine, carotene, carotenoid, choline, chlorogenic acid, cholic acid, chondroitin sulfate, chondroitin sulfate, cholestan, chrysin, coenzyme Q10, conjugated linoleic acid, corosolic acid, creatine, dehydroepiandrosterone, dichlorophen, diindolymethane, dimethylglycine, dimercapto succinic acid, ebselen, ellagic acid, enzymes, fisetin, formononetin, glucaric acid (glucarate), glucosamine (HCl or sulfate), glucosamine (N-acetyl), glutathione, hesperidine, hydroxy-3-methylbutyric acid, 5-hydroxytryptophan, indole-3-carbinol, inositol, isothiocyanates, linolenic acid-gamma, lipoic acid (alpha), melatonin, methylsulfonylmethane, menthol, minerals, naringin, pancreatin, para-aminobenzoic acid, paraben (methyl or propyl), phenolics, phosphatidylcholine, phosphatidylserine, phospholipids, phytosterols, progesterone, pregnenolone, omega-3 fatty acids, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta, and gamma), zeaxanthin, gingko biloba, ginger, cat's claw, hypericum, aloe vera, evening primrose, garlic, ginseng, capsicum, dong quai, ginseng, feverfew, fenugreek, echinacea, green tea, marshmallow, saw palmetto, tea tree oil, fish oil, psyllium, kava-kava, licorice root, mahonia aquifolium, hawthorne, tumeric, witch Hazel, yohimbe, aleurain, mistletoe, bilberry, bee pollen, peppermint oil, beta-carotene, genistein, lutein, lycopene, polyphenols, *Bifidobacterium infantis* 35624, *Bifidobacterium lactis* HN019, *Lactobacillus reuteri* ATCC55730, *Lactobacillus rhamnosus, Lactobacillus casei* DN-114 001, *Bifidobacterium lactis* Bb-12, or mixtures or combinations thereof. In another aspect describe herein, the excipients comprise one or more flavorings, colorings, hygroscopic polymers, opacifiers, thickening agents, surfactants, or pharmaceutically acceptable excipients. In another aspect describe herein, the one or more active pharmaceutical ingredients comprises one or more of dextromethorphan hydrobromide, menthol, thymol, nicotine, nicotine polacrilex, bismuth subsalicylate, NSAIDS, or combinations thereof. In another aspect describe herein, the matrix is a liquid, flowable gel, or viscous semi-solid. In another aspect describe herein, the shell comprises: (a) about 20% to about 60% of one or more film-forming polymers; (b) about 30% to about 70% of one or more plasticizers; (c) about 0.5% to about 2% of one or more polymer modifiers; (d) about 0.1% to about 5% of one or more first sweeteners; and (e) about 10% to about 40% of one or more solvents. In another aspect describe herein, the matrix comprises: (a) about 30% to about 95% of one or more hydrophilic vehicles; (b) about 0.05% to about 5% of one or more second sweeteners; (c) about 0.01% to about 6% of one or more flavors; (d) about 1% to about 20% one or more solvents; and (e) about 0.05% to about 60% of one or more active pharmaceutical ingredients. In another aspect describe herein, the shell comprises: (a) about 35% of one or more film-forming polymers; (b) about 37% of one or more plasticizers; (c) about 0.5% of one or more polymer modifiers; (d) about 2.7% of one or more first sweeteners; and (e) about 21% of one or more solvents. In another aspect describe herein, the ratio of the active pharmaceutical ingredient to a combined weight percentage of the hydrophilic vehicle, flavor, sweetener, solvent, and excipient is about 1:0.5 to about 1:500.

Another embodiment described herein is method for treating, retarding the progression of, prophylaxis of, delaying the onset of, ameliorating, reducing the symptoms of, or promoting health, including but not limited to of one or more of pain, inflammation, cough, cold, sinusitis, throat or bronchial irritation, fever, flu, inflammation of the gastrointestinal tract, neoplasia, hyperthyroidism, hypercalcemia, hyperparathyroidism, parathyroid carcinoma, indigestion, heartburn, irritable bowels, constipation, diarrhea, insomnia, dry mouth, halitosis, stained teeth, oral pain, loss of enamel, cessation of urge to smoke, fatigue, or malaise comprising administering to a subject in need thereof any of the oral pharmaceutical compositions described herein.

Another embodiment described herein is a composition for treating, retarding the progression of, prophylaxis of, delaying the onset of, ameliorating, reducing the symptoms of, or promoting health, including but not limited to of one or more of pain, inflammation, cough, cold, chest congestion, nasal congestion, sinusitis, throat or bronchial irritation, allergies, fever, flu, inflammation of the gastrointestinal tract, sour stomach, neoplasia, hyperthyroidism, hypercalcemia, hyperparathyroidism, parathyroid carcinoma, indigestion, heartburn, irritable bowels, constipation, diarrhea, insomnia, dry mouth, mouth odor, halitosis, stained teeth, oral pain, loss of enamel, nicotine desire; cessation of urge to smoke, fatigue, or malaise comprising administering to a subject in need thereof any of the oral pharmaceutical compositions described herein.

Another embodiment described herein is a pharmaceutical composition comprising a soft dosage form comprising a shell encapsulating a liquid matrix, wherein the shell comprises: (a) about 20% to about 60% of one or more film-forming polymers; (b) about 30% to about 70% of one or more plasticizers; (c) about 0.5% to about 2% of one or more polymer modifiers; (d) about 0.1% to about 5% of one or more first sweeteners; (e) about 10% to about 40% of one or more solvents; and the matrix comprises: (f) about 30% to about 95% of one or more hydrophilic vehicles; (g) about 0.05% to about 5% of one or more second sweeteners; (h) about 0.01% to about 6% of one or more flavors; (i) about 1% to about 20% water; and (j) about 0.05% to about 60% of one or more active pharmaceutical ingredients.

Another embodiment described herein is a method of delivering an active pharmaceutical ingredient to a patient population unable to receive a conventional dosage form comprising administering to the patient the oral pharmaceutical composition comprising a soft dosage form as described herein.

Another embodiment described herein is a composition for delivering an active pharmaceutical ingredient to a patient population unable to receive a conventional dosage form comprising administering to the patient in need thereof an oral pharmaceutical composition comprising a soft dosage form as described herein.

Another embodiment described herein is a pharmaceutical combination comprising any of the compositions described herein and one or more additional therapeutic compounds. In one aspect describe herein, the one or more additional therapeutic compounds comprises one or more of NSAIDS, diphenhydramine, codeine, chlorhexidine, cimetidine, ranitidine, famotidine, ondansetron, omeprazole, lansoprazole, rabeprazole, esomeprazole, pantoprazole, calcium supplements, magnesium hydroxide, bupropion, or varenicline.

Another embodiment described herein is a method for treating for treating, retarding the progression of, prophylaxis of, delaying the onset of, ameliorating, reducing the symptoms of, or promoting health, including but not limited to of one or more of pain, inflammation, cough, cold, chest congestion, nasal congestion, sinusitis, throat or bronchial irritation, allergies, fever, flu, inflammation of the gastrointestinal tract, sour stomach, neoplasia, hyperthyroidism, hypercalcemia, hyperparathyroidism, parathyroid carcinoma, indigestion, heartburn, irritable bowels, constipation, diarrhea, insomnia, dry mouth, mouth odor, halitosis, stained teeth, oral pain, loss of enamel, nicotine desire; cessation of urge to smoke, fatigue, or malaise comprising administering to a subject in need thereof any of the pharmaceutical combinations described herein.

Another embodiment described herein is a method for manufacturing an oral pharmaceutical composition comprising the steps of: (a) preparing a gel mass composition where the composition comprises one or more film forming polymers, one or more plasticizers, one or more sweeteners, one or more excipients in one or more solvents; (b) mixing the first solution at least about 50° C. under vacuum for 1 to 2 hours; (c) preparing a gel fill composition comprising one or more hydrophilic vehicles, one or more flavors, one or more sweeteners, one or more excipients, one or more active pharmaceutical ingredients in one or more solvents; (d) mixing the second solution at least about 50° C.; (e) casting the gel composition into films or ribbons using heat-controlled drums or surfaces; and (f) forming a soft dosage form comprising a liquid matrix fill using rotary die encapsulation technology.

Another embodiment described herein is an oral pharmaceutical composition comprising a soft dosage form comprising an active pharmaceutical ingredient in a liquid matrix produced by any of the methods described herein. In one aspect described herein, the dosage form is stable for at 25° C. for at least one year.

Another embodiment described herein is a kit for dispensing any of the oral pharmaceutical compositions described herein comprising: (a) at least one oral pharmaceutical composition; (b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally (c) at least one daily regimen for the oral pharmaceutical composition; and (d) an insert comprising instructions or prescribing information for the oral pharmaceutical composition. In one aspect described herein, the kit is useful for treating pain, inflammation, cough, cold, chest congestion, nasal congestion, sinusitis, throat or bronchial irritation, allergies, fever, flu, inflammation of the gastrointestinal tract, sour stomach, neoplasia, hyperthyroidism, hypercalcemia, hyperparathyroidism, parathyroid carcinoma, indigestion, heartburn, irritable bowels, constipation, diarrhea, insomnia, dry mouth, mouth odor, halitosis, stained teeth, oral pain, loss of enamel, nicotine desire; cessation of urge to smoke, fatigue, or malaise according to any of the methods described herein.

Another embodiment described herein is an oral pharmaceutical composition suitable for chewing, sucking, or buccal dissolution comprising a shell encapsulating a matrix, the shell comprising: (a) one or more film-forming polymers; (b) one or more plasticizers; (c) one or more polymer modifiers; (d) one or more first sweeteners; (e) one or more first solvents; and (f) optionally, one or more excipients; and the matrix comprising: (g) one or more hydrophilic vehicles; (h) one or more flavors; (i) one or more second sweeteners; (j) one or more second solvents; (k) dextromethorphan hydrobromide; (l) menthol; and (m) optionally, one or more excipients. In one aspect described herein, the film-forming polymer comprises one or more of gelatin, partially hydrolyzed gelatin, hydrolyzed gelatin, hydrolyzed collagen, or combinations thereof. In another aspect described herein, the plasticizer comprises one or more of glycerol, maltitol, mannitol, xylitol, lycasin, or combinations thereof. In another aspect described herein, the polymer modifier comprises one or more of citric acid, acetic acid, lactic acid, malic acid, tartaric acid, or combinations thereof. In another aspect described herein, the hydrophilic vehicle comprises propylene glycol, polyethylene glycol 400, polyvinylpyrrolidone K30, glycerin, sorbitol, xylitol, maltitol, or combinations thereof. In another aspect described herein, the first sweetener comprises sucralose, aspartame, stevia, acesulfame potassium, xylitol, or combinations thereof. In another aspect described herein, the flavoring comprises citric acid, lactic acid, sodium citrate, orange flavor, menthol, eucalyptol, peppermint oil, methyl salicylate, glycine, or combinations thereof. In another aspect described herein, the second sweetener comprises mannitol, maltitol, xylitol, thaumatin, glycyrrhizic acid salts, acesulfame potassium, acesulfame salts, sucralose, aspartame, stevia, or combinations thereof. In another aspect described herein, the excipients comprise one or more flavorings, colorings, hygroscopic polymers, opacifiers, thickening agents, surfactants, or pharmaceutically acceptable excipients. In another aspect described herein, the matrix is a liquid, flowable gel, or viscous semi-solid. In another aspect described herein, the shell comprises: (a) about 10% to about 80% of one or more film-forming polymers; (b) about 20% to about 70% of one or more plasticizers; (c) about 0.01% to about 5% of one or more polymer modifiers; (d) about 0.1% to about 5% of one or more first sweeteners; (e) about 5% to about 50% of one or more first solvents; (f) optionally, one or more excipients; and the matrix comprises: (g) about 40% to about 99% of one or more hydrophilic vehicles; (h) about 0.5% to about 10% of one or more flavors; (i) about 0.5% to about 5% of one or more second sweeteners; (j) about 1% to about 20% of one or more second solvents; (k) about 0.1% to about 5% of dextromethorphan hydrobromide; (l) about 0.05% to about 1% of menthol; and (m) optionally, one or more excipients. In another aspect described herein, the shell comprises: (a) about 10% to about 50% gelatin, 150 Bloom; (b) about 1% to about 20% gelatin, 100 Bloom; (c) about 1% to about 10% hydrolyzed collagen; (d) about 10% to about 20% lycasin; (e) about 10% to about 50% glycerin; (f) about 0.1% to about 2% citric acid; (g) about 0.1% to about 5% xylitol; (h) about 0.1% to about 1% sucralose; and (i) about 10% to about 50% water. In another aspect described herein, the matrix comprises: (a) about 10% to about 40% polyethylene glycol 400; (b) about 1% to about 15% propylene glycol; (c) about 0.1% to about 5% polyvinylpyrrolidone K30; (d) about 25% to about 75% lycasin; (e) about 0.1% to about 5% citric acid; (f) about 0.1% to about 5% lactic acid; (g) about 0.1% to about 5% sucralose; (h) about 0.1% to about 5% acesulfame potassium; (i) about 1% to about 10% water; (j) about 0.1% to about 5% dextromethorphan hydrobromide; and (k) about 0.05% to about 1% menthol. In another aspect described herein, the shell comprises: (a) about 20% gelatin, 150 Bloom; (b) about 9% gelatin, 100 Bloom; (c) about 5% hydrolyzed collagen; (d) about 17% lycasin; (e) about 25% glycerin; (f) about 0.5% citric acid; (g) about 2.5% about xylitol; (h) about 0.2% sucralose; and (i) about 21% water; and the matrix comprises: (j) about 21% polyethylene glycol 500; (k) about 8% propylene glycol; (l) about 1% polyvinylpyrrolidone K30; (m) about 58% lycasin; (n) about 1% citric acid; (o) about 1% lactic acid; (p) about 0.6% sucralose; (q) about 0.6% acesulfame potassium; (r) about 5% water; (s) about 1% dextromethorphan hydrobromide; and (t) about 0.1% menthol. In another aspect described herein, the ratio of the active pharmaceutical ingredient to a combined weight percentage of the hydrophilic vehicle, flavor, sweetener, solvent, and excipient is about 1:50 to about 1:200.

Another embodiment described herein is a method for treating, retarding the progression of, prophylaxis of, delaying the onset of, ameliorating, or reducing the symptoms of, or promoting health, including but not limited to of one or more of inflammation, cough, cold, chest congestion, nasal congestion, sinusitis, throat or bronchial irritation, flu, fever, or pain comprising administering to a subject in need thereof any of the oral pharmaceutical compositions described herein.

Another embodiment described herein is a composition for treating, retarding the progression of, prophylaxis of, delaying the onset of, ameliorating, reducing the symptoms of, or promoting health, including but not limited to of one or more of, inflammation, cough, cold, chest congestion, nasal congestion, sinusitis, throat or bronchial irritation, flu, fever, or pain comprising administering to a subject in need thereof any of the oral pharmaceutical compositions described herein.

Another embodiment described herein is a pharmaceutical composition comprising a soft dosage form comprising a shell encapsulating a liquid matrix, wherein the shell comprises: (a) about 10% to about 50% gelatin, 150 Bloom; (b) about 1% to about 20% gelatin, 100 Bloom; (c) about 1% to about 10% hydrolyzed collagen; (d) about 10% to about 20% lycasin; (e) about 10% to about 50% glycerin; (f) about 0.1% to about 2% citric acid; (g) about 0.1% to about 5% xylitol; (h) about 0.1% to about 1% sucralose; and (i) about 10% to about 50% water; and the matrix comprises: (j) about 10% to about 40% polyethylene glycol 400; (k) about 1% to about 15% propylene glycol; (l) about 0.1% to about 5% polyvinylpyrrolidone K30; (m) about 25% to about 75% lycasin; (n) about 0.1% to about 5% citric acid; (o) about 0.1% to about 5% lactic acid; (p) about 0.1% to about 5% sucralose; (q) about 0.1% to about 5% acesulfame potassium; (r) about 1% to about 10% water; (s) about 0.1% to about 5% dextromethorphan hydrobromide; and (t) about 0.05% to about 1% menthol.

Another embodiment described herein is a method of delivering an active pharmaceutical ingredient to a patient population unable to receive a conventional dosage form comprising administering to the patient any of the oral pharmaceutical compositions described herein.

Another embodiment described herein is a composition for delivering an active pharmaceutical ingredient to a patient population unable to receive a conventional dosage form comprising administering to the patient in need thereof any of the oral pharmaceutical compositions described herein.

Another embodiment described herein is a pharmaceutical combination comprising any one of the compositions described herein and one or more additional therapeutic compounds. In one aspect described herein, the one or more additional therapeutic compound comprises one or more of NSAID S, diphenhydramine, or codeine.

Another embodiment described herein is a method for treating for treating, retarding the progression of, prophylaxis of, delaying the onset of, ameliorating, reducing the symptoms of, or promoting health, including but not limited to of one or more of inflammation, cough, cold, chest congestion, nasal congestion, sinusitis, throat or bronchial irritation, flu, fever, or pain comprising administering to a subject in need thereof any of the pharmaceutical combinations described herein.

Another embodiment described herein is a pharmaceutical dosage form for treating one or more of inflammation, cough, cold, chest congestion, nasal congestion, sinusitis, throat or bronchial irritation, flu, fever, or pain comprising any of the pharmaceutical compositions described herein.

Another embodiment described herein is a method for treating inflammation, cough, cold, chest congestion, nasal congestion, sinusitis, throat or bronchial irritation, flu, fever, or pain comprising administering one or more dosage forms comprising any of the pharmaceutical compositions described herein.

Another embodiment described herein is a means for treating inflammation, cough, cold, chest congestion, nasal congestion, sinusitis, throat or bronchial irritation, flu, fever, or pain comprising administering one or more dosage forms comprising any of the pharmaceutical compositions described herein.

Another embodiment described herein is a method for manufacturing the oral pharmaceutical composition comprising the steps of: (a) preparing a gel fill composition comprising a first solution and a second solution wherein: (i) the first solution comprises polyvinylpyrrolidone K30, orange flavor, citric acid, sucralose, acesulfame potassium, lycasin and water, one or more excipients in one or more solvents and mixed at a temperature no greater than 55° C. until dissolved and clear; (ii) the second solution comprises polyethylene glycol 400, propylene glycol and lactic acid and mixed until dissolved and clear; where the composition comprises one or more film forming polymers, one or more plasticizers, one or more sweeteners, one or more excipients in one or more solvents; (iii) adding dextromethorphan hydrobromide and menthol to the second solution and mixing the first solution and heating to no greater than 55° C. until dissolved; and (iv) combining the first solution with the second solution and purging with nitrogen; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a soft dosage form comprising an active pharmaceutical ingredient in a liquid matrix produced by any of the methods described herein. In one aspect described herein, the dosage form is stable for at least 1 year at 25° C.

Another embodiment described herein is an oral pharmaceutical composition suitable for chewing, sucking, or buccal dissolution comprising a shell encapsulating a matrix, the shell comprising: (a) one or more film-forming polymers; (b) one or more plasticizers; (c) one or more polymer modifiers; (d) one or more first sweeteners; (e) one or more first solvents; and (f) optionally, one or more excipients; and the matrix comprising: (g) one or more hydrophilic vehicles; (h) one or more flavors; (i) one or more second sweeteners; (j) one or more second solvents; (k) thymol; (l) menthol; and (m) optionally, one or more excipients. In one aspect described herein, the film-forming polymer comprises one or more of gelatin, partially hydrolyzed gelatin, hydrolyzed gelatin, hydrolyzed collagen, or combinations thereof. In another aspect described herein, the plasticizer comprises one or more of glycerol, maltitol, mannitol, xylitol, lycasin, or combinations thereof. In another actic acid, malic acid, tartaric acid, or combinations thereof. In another aspect described herein, the hydrophilic vehicle comprises propylene glycol, polyethylene glycol 400, polyvinylpyrrolidone K30, glycerin, sorbitol, xylitol, maltitol, or combinations thereof. In another aspect described herein, the first sweetener comprises sucralose, aspartame, stevia, acesulfame potassium, xylitol, or combinations thereof. In another aspect described herein, the flavoring comprises citric acid, lactic acid, sodium citrate, orange flavor, eucalyptol, peppermint oil, methyl salicylate, glycine, or combinations thereof. In another aspect described herein, the second sweetener comprises mannitol, maltitol, xylitol, thaumatin, glycyrrhizic acid salts, acesulfame potassium, acesulfame salts, sucralose, aspartame, stevia, or combinations thereof. In another aspect described herein, the excipients comprise one or more flavorings, colorings, hygroscopic polymers, opacifiers, thickening agents, surfactants, or pharmaceutically acceptable excipients. In another aspect described herein, the matrix is a liquid, flowable gel, or viscous semi-solid. In another aspect described herein, the shell comprises: (a) about 10% to about 80% of one or more film-forming polymers; (b) about 20% to about 70% of one or more plasticizers; (c) about 0.01% to about 5% of one or more polymer modifiers; (d) about 0.1% to about 5% of one or more first sweeteners; (e) about 5% to about 50% of one or more first solvents; and (f) optionally, one or more excipients; and the matrix comprises: (g) about 50% to about 99% of one or more hydrophilic vehicles; (h) about 0.01% to about 5% of one or more flavors; (i) about 0.01% to about 5% of one or more second sweeteners; (j) about 1% to about 20% of one or more second solvents; (k) about 0.001% to about 1% of thymol; (l) about 0.05% to about 1% of menthol; and (m) optionally, one or more excipients. In another aspect described herein, the shell comprises: (a) about 10% to about 40% gelatin, 100 Bloom; (b) about 1% to about 10% hydrolyzed collagen; (c) about 10% to about 30% lycasin; (d) about 10% to about 40% glycerin; (e) about 1% to about 10% propylene glycol; (f) about 0.05% to about 2% citric acid; (g) about 1% to about 5% xylitol; (h) about 0.05% to about 2% sucralose; (i) about 0.05% to about 2% peppermint oil; and (j) about 10% to about 40% water. In another aspect described herein, the matrix comprises: (a) about 30% to about 60% glycerin; (b) about 0.05% to about 5% propylene glycol; (c) about 0.1% to about 5% polyvinylpyrrolidone K30; (d) about 20% to about 60% sorbitol; (e) about 0.1% to about 5% citric acid; (f) about 0.1% to about 5% sucralose; (g) about 0.025% to about 2% eucalyptol; (h) about 0.05% to about 2% peppermint oil; (i) about 1% to about 20% water; (j) about 0.001% to about 0.01% thymol; and (k) about 0.05% to about 3% menthol. In another aspect described herein, the shell comprises: (a) about 27% gelatin, 100 Bloom; (b) about 5% hydrolyzed collagen; (c) about 17% lycasin; (e) about 21% glycerin; (f) about 1% propylene glycol; (g) about 0.5% citric acid; (h) about 2.5% xylitol; (i) about 0.8% sucralose; (j) about 0.1% peppermint oil; (k) about 24% water; and the matrix comprises: (l) about 42% glycerin; (m) about 2% propylene glycol; (n) about 3% polyvinylpyrrolidone K30; (o) about 40% sorbitol; (p) about 0.3% citric acid; (q) about 0.5% sucralose; (r) about 0.1% eucalyptol; (s) about 0.3% peppermint oil; (t) about 10% water; (u) about 0.004% thymol; and (v) about 0.2% menthol. In another aspect described herein, the ratio of the active pharmaceutical ingredient to a combined weight percentage of the hydrophilic vehicle, flavor, sweetener, solvent, and excipient is about 1:250 to about 1:1000.

Another embodiment described herein is a method for treating, retarding the progression of, prophylaxis of, delaying the onset of, ameliorating, or reducing the symptoms of, or promoting health, including but not limited to of one or more of dry mouth, halitosis, stained teeth, oral pain, loss of enamel, refreshing breath, inhibiting onset of breath malodor, or freshening the oral cavity comprising administering to a subject in need thereof any of the oral pharmaceutical compositions described herein.

Another embodiment described herein is a composition for treating, retarding the progression of, prophylaxis of, delaying the onset of, ameliorating, reducing the symptoms of, or promoting health, including but not limited to of one or more of dry mouth, halitosis, stained teeth, oral pain, loss of enamel, refreshing breath, inhibiting onset of breath malodor, or freshening the oral cavity comprising administering to a subject in need thereof any of the oral pharmaceutical compositions described herein.

Another embodiment described herein is a pharmaceutical composition comprising a soft dosage form comprising a shell encapsulating a liquid matrix, wherein the shell comprises: (a) about 10% to about 40% gelatin, 100 Bloom; (b) about 1% to about 10% hydrolyzed collagen; (c) about 10% to about 30% lycasin; (d) about 10% to about 40% glycerin; (e) about 1% to about 10% propylene glycol; (f) about 0.05% to about 2% citric acid; (g) about 1% to about 5% xylitol; (h) about 0.05% to about 2% sucralose; (i) about 0.05% to about 2% peppermint oil; and (j) about 10% to about 40% water; and the matrix comprises: (k) about 30% to about 60% glycerin; (l) about 0.05% to about 5% propylene glycol; (m) about 0.1% to about 5% polyvinylpyrrolidone K30; (n) about 20% to about 60% sorbitol; (o) about 0.1% to about 5% citric acid; (p) about 0.1% to about 5% sucralose; (q) about 0.025% to about 2% eucalyptol; (r) about 0.05% to about 2% peppermint oil; (s) about 1% to about 20% water; (t) about 0.001% to about 0.01% thymol; and (u) about 0.05% to about 3% menthol.

Another embodiment described herein is a method of delivering an active pharmaceutical ingredient to a patient population unable to receive a conventional dosage form comprising administering to the patient the oral pharmaceutical composition comprising any of the soft dosage forms described herein.

Another embodiment described herein is a composition for delivering an active pharmaceutical ingredient to a patient population unable to receive a conventional dosage form comprising administering to the patient in need thereof an oral pharmaceutical composition comprising any of the soft dosage forms described herein.

Another embodiment described herein is a pharmaceutical combination comprising any one of the compositions described herein and one or more additional therapeutic compounds. In one aspect described herein, the one or more additional therapeutic compounds comprises chlorhexidine or ethanol.

Another embodiment described herein is a method for treating for treating, retarding the progression of, prophylaxis of, delaying the onset of, ameliorating, reducing the symptoms of, or promoting health, including but not limited to of one or more of dry mouth, halitosis, stained teeth, oral pain, loss of enamel, refreshing breath, inhibiting onset of breath malodor, or freshening the oral cavity comprising administering to a subject in need thereof any of the pharmaceutical combinations described herein.

Another embodiment described herein is a pharmaceutical dosage form for refreshing breath, inhibiting onset of breath malodor, treating halitosis, or freshening the oral cavity comprising any of the pharmaceutical compositions described herein.

Another embodiment described herein is a method for refreshing breath, inhibiting onset of breath malodor, treating halitosis, or freshening the oral cavity comprising administering one or more dosage forms comprising any of the pharmaceutical compositions described herein.

Another embodiment described herein is a means for refreshing breath, inhibiting onset of breath malodor, treating halitosis, or freshening the oral cavity comprising administering one or more dosage forms comprising any of the pharmaceutical compositions described herein.

Another embodiment described herein is a method for manufacturing an oral pharmaceutical composition comprising the steps of: (a) preparing a gel fill composition comprising a first gel fill solution and a second gel fill solution, wherein (i) the first gel fill solution comprises one or more hydrophilic vehicle, sweetener, flavor, thymol, in one or more solvents and is mixed at a temperature between 30-50° C. until dissolved; (ii) the second gel fill solution comprises one or more hydrophilic vehicles and menthol and is mixed at a temperature between 30-50° C. until dissolved; and (iv) combining the first gel fill solution and the second gel fill solution, adding flavor and mixing for at least 25 minutes; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a soft dosage form comprising an active pharmaceutical ingredient in a liquid matrix produced by any of the methods described herein. In one aspect described herein, the dosage form is stable for at least 1 year at 25° C.

Another embodiment described herein is an oral pharmaceutical composition suitable for chewing, sucking, or buccal dissolution comprising a shell encapsulating a matrix, the shell comprising: (a) one or more film-forming polymers; (b) one or more plasticizers; (c) one or more polymer modifiers; (d) one or more first sweeteners; (e) one or more first solvents; and (f) optionally, one or more excipients; and the matrix comprising: (g) one or more hydrophilic vehicles; (h) one or more flavors; (i) one or more second sweeteners; (j) one or more second solvents; (k) nicotine polacrilex; and (l) optionally, one or more excipients. In one aspect described herein, the film-forming polymer comprises one or more of gelatin, partially hydrolyzed gelatin, hydrolyzed gelatin, hydrolyzed collagen, or combinations thereof. In another aspect described herein, the plasticizer comprises one or more of glycerol, maltitol, mannitol, xylitol, lycasin, or combinations thereof. In one aspect described herein, the polymer modifier comprises one or more of citric acid, acetic acid, lactic acid, malic acid, tartaric acid, or combinations thereof. In one aspect described herein, the hydrophilic vehicle comprises propylene glycol, polyethylene glycol 400, polyvinylpyrrolidone K30, glycerin, sorbitol, xylitol, maltitol, or combinations thereof. In one aspect described herein, the first sweetener comprises sucralose, aspartame, stevia, acesulfame potassium, xylitol, or combinations thereof. In one aspect described herein, the flavoring comprises citric acid, lactic acid, sodium citrate, orange flavor, eucalyptol, peppermint oil, methyl salicylate, glycine, or combinations thereof. In one aspect described herein, the second sweetener comprises mannitol, maltitol, xylitol, thaumatin, glycyrrhizic acid salts, acesulfame potassium, acesulfame salts, sucralose, aspartame, stevia, or combinations thereof. In one aspect described herein, the excipients comprise one or more flavorings, colorings, hygroscopic polymers, opacifiers, thickening agents, surfactants, or pharmaceutically acceptable excipients. In one aspect described herein, the matrix is a liquid, flowable gel, or viscous semi-solid. In one aspect described herein, the shell comprises: (a) about 20% to about 80% of one or more film-forming polymers; (b) about 20% to about 70% of one or more plasticizers; (c) about 0.01% to about 5% of one or more polymer modifiers; (d) about 0.1% to about 5% of one or more first sweeteners; (e) about 5% to about 50% of one or more first solvents; (f) optionally, one or more excipients; and the matrix comprises: (g) about 30% to about 80% of one or more hydrophilic vehicles; (h) about 0.5% to about 10% of one or more flavors; (i) about 0.01% to about 5% of one or more second sweeteners; (j) about 1% to about 30% of one or more second solvents; (k) about 0.1% to about 5% of nicotine polacrilex; and (m) optionally, one or more excipients. In one aspect described herein, the shell comprises: (a) about 10% to about 40% gelatin, 150 Bloom; (b) about 1% to about 20% gelatin, 100 Bloom; (c) about 1% to about 10% gelatin hydrolysate; (d) about 10% to about 40% glycerin; (e) about 10% to about 40% maltitol; (f) about 0.05% to about 2% citric acid; (g) about 1% to about 5% xylitol; (h) about 0.05% to about 2% sucralose; (i) about 0.05% to about 2% peppermint oil; and (j) about 10% to about 40% water. In another aspect described herein, the matrix comprises: (a) about 0.05% to about 5% polyethylene glycol 400; (b) about 10% to about 40% glycerin; (c) about 0.1% to about 5% xylitol; (d) about 10% to about 60% maltitol; (e) about 0.1% to about 10% glycine; (f) about 0.1% to about 5% sucralose; (g) about 0.025% to about 2% menthol; (h) about 0.025% to about 2% peppermint oil; (i) about 1% to about 30% water; and (j) about 0.01% to about 5% nicotine polacrilex. In another aspect described herein, the shell comprises: (a) about 22% gelatin, 150 Bloom; (b) about 10% gelatin, 100 Bloom; (c) about 5% gelatin hydrolysate; (d) about 20% glycerin; (e) about 17% maltitol; (f) about 0.5% citric acid; (g) about 2.6% xylitol; (h) about 0.2% sucralose; (i) about 0.3% peppermint oil; and (j) about 21% water; and the matrix comprises: (k) about 1% polyethylene glycol 400; (l) about 19% glycerin; (m) about 3% xylitol; (n) about 37% maltitol; (o) about 5% glycine; (p) about 0.2% sucralose; (q) about 0.04% menthol; (r) about 0.04% peppermint oil; (s) about 17% water; and (t) about 2% nicotine polacrilex. In another aspect described herein, the ratio of the active pharmaceutical ingredient to a combined weight percentage of the hydrophilic vehicle, flavor, sweetener, solvent, and excipient is about 1:10 to about 1:100.

Another embodiment described herein is a method for treating, retarding the progression of, prophylaxis of, delaying the onset of, ameliorating, or reducing the symptoms of, or promoting health, including but not limited to cessation of urge to smoke, satiating nicotine desire, nicotine-replacement therapy, or smoking cessation therapy comprising administering to a subject in need thereof any of the oral pharmaceutical compositions described herein.

Another embodiment described herein is a composition for treating, retarding the progression of, prophylaxis of, delaying the onset of, ameliorating, reducing the symptoms of, or promoting health, including but not limited to cessation of urge to smoke, satiating nicotine desire, nicotine-replacement therapy, or smoking cessation therapy comprising administering to a subject in need thereof any of the oral pharmaceutical compositions described herein.

Another embodiment described herein is a pharmaceutical composition comprising a soft dosage form comprising a shell encapsulating a liquid matrix, wherein the shell comprises: (a) about 10% to about 40% gelatin, 150 Bloom; (b) about 1% to about 20% gelatin, 100 Bloom; (c) about 1% to about 10% gelatin hydrolysate; (d) about 10% to about 40% glycerin; (e) about 10% to about 40% maltitol; (f) about 0.05% to about 2% citric acid; (g) about 1% to about 5% xylitol; (h) about 0.05% to about 2% sucralose; (i) about 0.05% to about 2% peppermint oil; and (j) about 10% to about 40% water; and the matrix comprises: (k) about 0.05% to about 5% polyethylene glycol 400; (l) about 10% to about 40% glycerin; (m) about 0.1% to about 5% xylitol; (n) about 10% to about 60% maltitol; (o) about 0.1% to about 10% glycine; (p) about 0.1% to about 5% sucralose; (q) about 0.025% to about 2% menthol; (r) about 0.025% to about 2% peppermint oil; (s) about 1% to about 30% water; and (t) about 0.01% to about 5% nicotine polacrilex.

Another embodiment described herein is a method of delivering an active pharmaceutical ingredient to a patient population unable to receive a conventional dosage form comprising administering to the patient the oral pharmaceutical composition comprising any of the soft dosage forms described herein.

Another embodiment described herein is a composition for delivering an active pharmaceutical ingredient to a patient population unable to receive a conventional dosage form comprising administering to the patient in need thereof an oral pharmaceutical composition comprising any of the soft dosage forms described herein.

Another embodiment described herein is a pharmaceutical combination comprising any of the compositions described herein and one or more additional therapeutic compounds. In one aspect described herein, the one or more additional therapeutic compound comprises bupropion or varenicline.

Another embodiment described herein is a method for treating for treating, retarding the progression of, prophylaxis of, delaying the onset of, ameliorating, reducing the symptoms of, or promoting health, including but not limited to cessation of urge to smoke, satiating nicotine desire, nicotine-replacement therapy, or smoking cessation therapy comprising administering to a subject in need thereof any of the pharmaceutical combinations described herein.

Another embodiment described herein is a pharmaceutical dosage form for satiating nicotine desire, nicotine-replacement therapy, or smoking cessation therapy comprising any of the pharmaceutical compositions described herein.

Another embodiment described herein is a method for satiating nicotine desire, nicotine-replacement therapy, or smoking cessation therapy comprising administering one or more dosage forms comprising any of the pharmaceutical compositions described herein.

Another embodiment described herein is a means for satiating nicotine desire, nicotine-replacement therapy, or smoking cessation therapy comprising administering one or more dosage forms comprising any of the pharmaceutical compositions described herein.

Another embodiment described herein is a method for manufacturing an oral pharmaceutical composition comprising the steps of: (a) preparing a gel fill composition comprising a first solution, a flavor solution, and a sweetener solution wherein: (i) the first solution comprises one or more hydrophilic vehicles, thickening agents, flavors, and excipients and is mixed at a temperature between 30-70° C. until dissolved; (ii) the flavor solution comprises one or more hydrophilic vehicle and flavor and is mixed at a temperature between 30-70° C. until dissolved; (iii) the sweetener solution comprises one or more sweetener in one or more solvents and nicotine and mixing until dissolved; and (iv) combining the first solution, flavor solution and sweetener solution and mixing to homogenize; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a soft dosage form comprising an active pharmaceutical ingredient in a liquid matrix produced by any of the methods described herein. In one aspect described herein, the dosage form is stable for at least 1 year at 25° C.

Another embodiment described herein is an oral pharmaceutical composition suitable for chewing, sucking, or buccal dissolution comprising a shell encapsulating a matrix, the shell comprising: (a) one or more film-forming polymers; (b) one or more plasticizers; (c) one or more polymer modifiers; (d) one or more first sweeteners; (e) one or more first solvents; and (f) optionally, one or more excipients; and the matrix comprising: (g) one or more hydrophilic vehicles; (h) one or more flavors; (i) one or more second sweeteners; (j) one or more second solvents; (k) bismuth subsalicylate; and (l) optionally, one or more excipients. In one aspect described herein, the film-forming polymer comprises one or more of gelatin, partially hydrolyzed gelatin, hydrolyzed gelatin, hydrolyzed collagen, or combinations thereof. In another aspect described herein, the plasticizer comprises one or more of glycerol, maltitol, mannitol, xylitol, lycasin, or combinations thereof. In another aspect described herein, the polymer modifier comprises one or more of citric acid, acetic acid, lactic acid, malic acid, tartaric acid, or combinations thereof. In another aspect described herein, the hydrophilic vehicle comprises propylene glycol, polyethylene glycol 400, polyvinylpyrrolidone K30, glycerin, sorbitol, xylitol, maltitol, or combinations thereof. In another aspect described herein, the first sweetener comprises sucralose, aspartame, stevia, acesulfame potassium, xylitol, or combinations thereof. In another aspect described herein, the flavoring comprises citric acid, lactic acid, sodium citrate, orange flavor, eucalyptol, peppermint oil, methyl salicylate, glycine, or combinations thereof. In another aspect described herein, the second sweetener comprises mannitol, maltitol, xylitol, thaumatin, glycyrrhizic acid salts, acesulfame potassium, acesulfame salts, sucralose, aspartame, stevia, or combinations thereof. In another aspect described herein, the excipients comprise one or more flavorings, colorings, hygroscopic polymers, opacifiers, thickening agents, surfactants, or pharmaceutically acceptable excipients. In another aspect described herein, the matrix is a liquid, flowable gel, or viscous semi-solid. In another aspect described herein, the shell comprises: (a) about 10% to about 50% of one or more film-forming polymers; (b) about 10% to about 60% of one or more plasticizers; (c) about 0.01% to about 5% of one or more polymer modifiers; (d) about 0.1% to about 5% of one or more first sweeteners; (e) about 5% to about 50% of one or more first solvents; and (f) optionally, one or more excipients; and the matrix comprises: (g) about 20% to about 70% of one or more hydrophilic vehicles; (h) about 0.05% to about 1% of one or more flavors; (i) about 0.25% to about 5% of one or more second sweeteners; (j) about 1% to about 20% of one or more second solvents; (k) about 20% to about 80% of bismuth subsalicylate; and (l) optionally, one or more excipients. In another aspect described herein, the shell comprises: (a) about 10% to about 40% gelatin, 150 Bloom; (b) about 1% to about 20% gelatin, 100 Bloom; (c) about 1% to about 10% gelatin hydrolysate; (d) about 10% to about 40% glycerin; (e) about 10% to about 40% maltitol; (f) about 0.05% to about 2% citric acid; (g) about 1% to about 5% xylitol; (h) about 0.05% to about 2% sucralose; and (i) about 10% to about 40% water. In another aspect described herein, the matrix comprises: (a) about 0.05% to about 5% polyethylene glycol 400; (b) about 0.5% to about 5% glycerin; (c) about 1% to about 15% propylene glycol; (d) about 10% to about 40% sorbitol; (e) about 0.1% to about 5% xylitol; (f) about 0.05% to about 5% sucralose; (g) about 0.025% to about 2% menthol; (h) about 0.025% to about 2% peppermint oil; (i) about 1% to about 20% water; and (j) about 20% to about 80% bismuth subsalicylate. In another aspect described herein, the shell comprises: (a) about 19% gelatin, 150 Bloom; (b) about 13% gelatin, 100 Bloom; (c) about 2% gelatin hydrolysate; (d) about 22% glycerin; (e) about 14% maltitol; (f) about 0.5% citric acid; (g) about 2.5% xylitol; (h) about 0.2% sucralose; and (i) about 29% water; and the matrix comprises: (j) about 1% polyethylene glycol 400; (k) about 2% glycerin; (l) about 6% propylene glycol; (m) about 27% sorbitol; (n) about 3% xylitol; (o) about 0.2% sucralose; (p) about 0.04% menthol; (q) about 0.04% peppermint oil; (r) about 11% water; and (s) about 47% bismuth subsalicylate. In another aspect described herein, the ratio of the active pharmaceutical ingredient to a combined weight percentage of the hydrophilic vehicle, flavor, sweetener, solvent, and excipient is about 1:0.01 to about 1:20.

Another embodiment described herein is a method for treating, retarding the progression of, prophylaxis of, delaying the onset of, ameliorating, or reducing the symptoms of, or promoting health, including but not limited to of one or more of inflammation of the gastrointestinal tract, neoplasia, hyperthyroidism, hypercalcemia, hyperparathyroidism, parathyroid carcinoma, indigestion, heartburn, nausea, flatulence, bloating, acid reflux, irritable bowels, constipation, diarrhea, comprising administering to a subject in need thereof any of the oral pharmaceutical compositions described herein.

Another embodiment described herein is a pharmaceutical composition comprising a soft dosage form comprising a shell encapsulating a liquid matrix, wherein the shell comprises: (a) about 10% to about 40% gelatin, 150 Bloom; (b) about 1% to about 20% gelatin, 100 Bloom; (c) about 1% to about 10% gelatin hydrolysate; (d) about 10% to about 40% glycerin; (e) about 10% to about 40% maltitol; (f) about 0.05% to about 2% citric acid; (g) about 1% to about 5% xylitol; (h) about 0.05% to about 2% sucralose; and (i) about 10% to about 40% water; and the matrix comprises: (j) about 0.05% to about 5% polyethylene glycol 400; (k) about 0.5% to about 5% glycerin; (l) about 1% to about 15% propylene glycol; (m) about 10% to about 40% sorbitol; (n) about 0.1% to about 5% xylitol; (o) about 0.05% to about 5% sucralose; (p) about 0.025% to about 2% menthol; (q) about 0.025% to about 2% peppermint oil; (r) about 1% to about 20% water; and (s) about 20% to about 80% bismuth subsalicylate.

Another embodiment described herein is a method of delivering an active pharmaceutical ingredient to a patient population unable to receive a conventional dosage form comprising administering to the patient the oral pharmaceutical composition comprising any of the soft dosage forms described herein.

Another embodiment described herein is a composition for delivering an active pharmaceutical ingredient to a patient population unable to receive a conventional dosage form comprising administering to the patient in need thereof an oral pharmaceutical composition comprising any of the soft dosage forms described herein.

Another embodiment described herein is a pharmaceutical combination comprising any of the compositions described herein and one or more additional therapeutic compounds. In one aspect described herein, the one or more additional therapeutic compound comprises one or more of cimetidine, ranitidine, famotidine, ondansetron, omeprazole, lansoprazole, rabeprazole, esomeprazole, pantoprazole, calcium supplements, calcium hydroxide, alluminum hydroxide, magnesium hydroxide, or combinations thereof.

Another embodiment described herein is a method for treating for treating, retarding the progression of, prophylaxis of, delaying the onset of, ameliorating, reducing the symptoms of, or promoting health, including but not limited to of one or more of one or more of inflammation of the gastrointestinal tract, neoplasia, hyperthyroidism, hypercalcemia, hyperparathyroidism, parathyroid carcinoma, indigestion, heartburn, nausea, flatulence, bloating, acid reflux, irritable bowels, constipation, diarrhea comprising administering to a subject in need thereof the pharmaceutical combination comprising administering to a subject in need thereof any of the oral pharmaceutical combinations described herein.

Another embodiment described herein is a pharmaceutical dosage form for treating or alleviating indigestion, heartburn, nausea, flatulence, bloating, acid reflux, diarrhea, or other discomforts of the stomach and gastrointestinal tract, comprising any of the pharmaceutical compositions described herein.

Another embodiment described herein is a method for treating or alleviating indigestion, heartburn, nausea, flatulence, bloating, acid reflux, diarrhea, or other discomforts of the stomach and gastrointestinal tract, comprising administering one or more dosage forms comprising any of the pharmaceutical compositions described herein.

Another embodiment described herein is a means for treating or alleviating indigestion, heartburn, nausea, flatulence, bloating, acid reflux, diarrhea, or other discomforts of the stomach and gastrointestinal tract, comprising administering one or more dosage forms comprising any of the pharmaceutical compositions described herein.

Another embodiment described herein is a method for manufacturing an oral pharmaceutical composition comprising the steps of: (a) preparing a gel fill composition comprising a color solution, a flavor solution and a gel solution wherein: (i) the color solution comprises one or more colors and excipient in one or more solvents and mixed at a temperature between 30-50° C. until dissolved; (ii) the flavor solution comprises one or more of plasticizer, menthol and flavor and mixed at a temperature between 30-50° C. until dissolved; (iii) the gel solution comprises soaking one or more film forming polymer, plasticizer, sweeteners in one or more solvents, then heated at a temperature between 30-70° C. until dissolved; (iv) combining the color solution, flavor solution, and gel solution and adding bismuth subsalicylate and mixing at a temperature of 20-60° C. until dissolved; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a soft dosage form comprising an active pharmaceutical ingredient in a liquid matrix produced by any of the methods described herein. In one aspect described herein, the dosage form is stable for at least 1 year at 25° C.

BRIEF DESCRIPTION OF THE DRAWINGS

Further advantageous features of the present disclosure will become more apparent with the following detailed description when taken with reference to the accompanying drawings, each according to an aspect of the present disclosure:

FIG. 1. Dissolution of a nicotine Liquisoft capsule.

DETAILED DESCRIPTION

Described herein are oral pharmaceutical compositions of comprising chewable, suckable, or dissolvable soft gel capsules with various flowable fill compositions.

The oral pharmaceutical compositions described herein are soft gel capsules, e.g., "LiquiSoft™" capsules, suitable for chewing, sucking, or buccal dissolution and having pleasing organoleptic properties comprising flowable or liquid matrix fills of a variety of active pharmaceutical ingredients, or combinations thereof, and methods for preparation thereof.

The term "pharmaceutical combination" as used herein refers to either a pharmaceutical composition comprising one or more active pharmaceutical ingredient and one or more second therapeutic compounds or a pharmaceutical composition comprising an active pharmaceutical ingredient coadministered with a second therapeutic compound.

The phrase "organoleptic properties" as used herein refers to the sensory aspects experienced by one or more subjects, including but not limited to, sight, smell, taste, mouth feel, moisture content/dryness, plasticity, chewability, dissolution, residue, and aftertaste.

The terms "active ingredient" or "active pharmaceutical ingredient" as used herein refer to a pharmaceutical agent, active ingredient, compound, or substance, compositions, or mixtures thereof, that provide a pharmacological, often beneficial, effect.

The terms "dosage" or "dose" as used herein denotes any forms of the active ingredient formulation that contain an amount sufficient to produce a therapeutic effect with a single administration. The dosage form described herein is for oral administration. The preferred oral dosage forms described herein are soft gelatin capsules or "soft gels."

The terms "active pharmaceutical ingredient load" or "drug load" as used herein refers to the quantity (mass) of the active pharmaceutical ingredient comprised in a single soft capsule fill.

The term "formulation" or "composition" as used herein refers to the drug in combination with pharmaceutically acceptable excipients. This term includes orally administrable formulations as well as formulations administrable by other means.

The term "titration" as used herein refers to the incremental increase in drug dosage to a level that provides the optimal therapeutic effect.

The term "treating" refers to administering a therapy in an amount, manner, or mode effective to improve a condition, symptom, or parameter associated with a disorder.

The term "conventional dosage from" means a tablet or pill.

The term "prophylaxis" refers to preventing or reducing the progression of a disorder, either to a statistically significant degree or to a degree detectable to one skilled in the art.

The term "substantially" as used herein means to a great or significant extent, but not completely.

As used herein, all percentages (%) refer to weight percent unless noted otherwise.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing" and the like mean "comprising."

The term "or" can be conjunctive or disjunctive.

One embodiment described herein, is an oral pharmaceutical composition comprising a chewable, suckable, or dissolvable soft capsule shell encapsulating a liquid matrix fill comprising one or more active pharmaceutical ingredients. In one embodiment described herein, the pharmaceutical composition comprises that shown in Table 1.

TABLE 1

| Exemplary Liquisoft Composition | |
| --- | --- |
| Exemplary Ingredients | % weight |
| Capsule Shell Formulation | |
| Polymer(s) | 20-60 |
| Plasticizer(s) | 30-70 |
| Polymer Modifier(s) | 0-2 |

TABLE 1-continued

| Exemplary Liquisoft Composition | |
| --- | --- |
| Exemplary Ingredients | % weight |
| Sweetener(s) | 0-50 |
| Solvent(s) | 10-40 |
| Excipients: flavorings, colorings, opacifiers, etc. | 0.1-10 |
| TOTAL | 100% |
| Matrix Fill Formulation | |
| Hydrophilic Vehicle(s) | 20-90 |
| Flavoring(s) | 0-10 |
| Sweetener(s) | 0-50 |
| Optional Excipient(s) | 0-25 |
| Solvent(s) | 0-25 |
| Active Pharmaceutical Ingredient(s) (APIs) | 0-60 |
| TOTAL | 100% |

One embodiment described herein is an oral pharmaceutical composition suitable for chewing, sucking, or buccal dissolution. In one embodiment, the composition comprises a gel mass suitable for forming soft gel capsules. In another embodiment, the composition comprises a liquid matrix fill. In one embodiment, the composition comprises a flowable gel matrix fill. In another embodiment, the composition comprises a viscous semi-solid matrix fill. In another embodiment, the composition comprises a soft gel capsule and a liquid matrix fill. In one embodiment, the pharmaceutical composition provides a "burst" of sweetened flavored liquid comprising one or more active pharmaceutical ingredients to the oral cavity when a subject manipulates the dosage form within the mouth. The subject may bite or chew the dosage form, suck the dosage form, or allow the dosage form to slowly dissolve in the oral cavity. Upon rupturing the gel capsule shell by chewing, sucking, or dissolution within the mouth, the liquid matrix is released and provides a burst of liquid sensation to the subject's oral cavity. The sensation may be sweet, flavored, cooling, or a combination thereof. One or more of these "sensations" can be used to mask poor tasting active pharmaceutical ingredients or provide soothing sensations to a subject's oral mucosa, sinuses, or throat, for example.

One embodiment described herein is a soft capsule shell comprising one or more film-forming polymers, one or more plasticizers, one or more polymer modifiers, one or more solvents, one or more sweeteners, and optionally, one or more pharmaceutically acceptable excipients, including but not limited to coloring agents, flavorings, opacifiers, hygroscopic polymers, thickening agents, surfactants or the like.

Chewable soft capsule shells are described in U.S. Pat. Nos. 6,258,380; 8,097,279; 8,241,665; 8,414,916; and 8,765,174, each of which is in incorporated by reference herein for such teachings.

Another embodiment described herein is a matrix fill comprising one or more hydrophilic vehicles, one or more sweeteners, one or more flavorings, one or more solvents, optionally, one or more excipients, and one or more active pharmaceutical ingredients. In one embodiment described herein, the composition comprises that shown in Table 2.

TABLE 2

Exemplary Liquisoft Composition

| Component | Exemplary Component | Weight Percentage (%) |
|---|---|---|
| Capsule Shell Formulation | | |
| Polymers | Gelatin, 150 Bloom | 10-40 |
| | Gelatin, 100 Bloom | 1-20 |
| | Gelatin Hydrolysate | 0-7 |
| | Hydrolyzed Collagen | 0-7 |
| Plasticizer(s) | Glycerol | 10-50 |
| | Maltitol (Lycasin®) | 1-30 |
| | Xylitol | 0-20 |
| Sweeteners | Sucralose | 0-5 |
| Polymer Modifier | Citrate | 0-2 |
| Solvent | Water | 10-40 |
| TOTAL | | 100% |
| Matrix Fill Formulation | | |
| Hydrophilic Vehicle | Propylene Glycol | 0-20 |
| | Polyethylene Glycol 400 | 10-50 |
| | Polyvinylpyrrolidone K30 | 0-2 |
| Flavors | Citric Acid | 0-3 |
| | Lactic Acid | 0-3 |
| | Sodium Citrate | 0-3 |
| Sweeteners | Maltitol (Lycasin®) | 20-70 |
| | Mannitol | 0-5 |
| | Sucralose | 0-2 |
| | Thaumatin (Talin®) | 0-5 |
| | Glycyrrhizic acid salts (MagnaSweet®) | 0-5 |
| Excipients | | 0-25 |
| Solvent | Water | 0-15 |
| Active Pharmaceutical Ingredients (API) | e.g., Dextromethorphan Hydrobromide | 0-15 |
| TOTAL | | 100% |

In one embodiment described herein, the soft capsule shell comprises one or more film-forming polymers. In one embodiment, the polymer comprises gelatin having a Bloom strength of about 50 to about 400 Bloom, hydrolyzed gelatin, gelatin hydrolysate, hydrolyzed collagen, sodium and calcium alginate; natural and modified starch and starch hydrolysates, pectins and amylopectins, cellulose derivatives, such as or hydroxypropylmethylcellulose (HPMC), methylcellulose, cellulose, or combinations thereof. In one aspect described herein, the polymer comprises one or more gelatins or gelatin hydrolysates.

Examples of gelatin compositions that are useful for the pharmaceutical compositions described herein comprise acid bone gelatin, pig skin gelatin, chicken skin gelatin, fish gelatin, acid hide gelatin, gelatin hydrolysate, lime bone gelatin, or combinations thereof. Gelatins can be classified as either Type A or Type B gelatin. Type A gelatin is derived from the acid hydrolysis of collagen (e.g., acid bone gelatin or pig skin gelatin), while Type B gelatin (e.g., lime bone gelatin) is derived from the alkaline hydrolysis of collagen. Traditionally, bovine bones and skins are used as raw materials for manufacturing Type A and Type B gelatin, while porcine skins are used extensively for manufacturing Type A gelatin. In addition, at neutral pH values, Type A gelatins (acid processed gelatins) are typically net cationic (e.g., isoelectric point of about 7-9) and Type B gelatins (alkali processed gelatins) are typically net anionic (e.g., isoelectric point of about 4.5-5.3). Type A gelatin typically has higher plasticity and elasticity than type B gelatin; type B gelatin typically has higher gel strength than type A gelatin.

The strength of gelatin compositions is typically defined by their Bloom strength or grade. The Bloom test determines the weight (in grams) needed by a 0.5-inch diameter probe to deflect the surface of a gel 4 mm without breaking it. The result is expressed as "Bloom" or "Bloom strength." The pharmaceutical compositions described herein utilize gelatins with Bloom strengths in the range of about 50 Bloom to about 400 Bloom, including each integer within the specified range. In one embodiment, Bloom strengths for pharmaceutical compositions described herein are about 50 Bloom to about 250 Bloom including each integer within the specified range. In some embodiments, the gelatin Bloom strength is about 50 Bloom, about 80 Bloom, about 100 Bloom, about 120 Bloom, about 150 Bloom, about 180 Bloom, about 200 Bloom, or about 250 Bloom. In one embodiment, the gelatin Bloom strength is 100 Bloom. In another embodiment, the gelatin Bloom strength is 150 Bloom. In another embodiment, the gelatin Bloom strength is 195 Bloom. In another embodiment, the gelatin Bloom strength is 200 Bloom. In another aspect, the one or more film-forming polymers comprise one or more of gelatin, partially hydrolyzed gelatin, hydrolyzed gelatin, or combinations thereof.

In one embodiment described herein, the one or more polymers comprise one or more gelatins having a Bloom of about 100. In another aspect, the one or more polymers comprise one or more gelatins having a Bloom of about 150. In another aspect, the one or more polymers comprise one or more of partially hydrolyzed gelatin, hydrolyzed gelatin, hydrolyzed collagen, or combinations thereof.

In another embodiment described herein, the soft capsule shell comprises one or more plasticizers. As used herein, a plasticizer is a substance, often a polyol, that provides flexibility and softens the capsule. In one embodiment, the plasticizer comprises one or more of glycerol, sorbitol, mannitol, maltitol (Lycasin®), xylitol (Xylisorb®), or combinations thereof. In one aspect, the plasticizer comprises glycerol, sorbitol, or combinations thereof. In one aspect, the plasticizer comprises glycerol, maltitol (Lycasin®), xylitol, or combinations thereof.

In another embodiment described herein, the soft capsule shell comprises one or more sweeteners. In one embodiment, the sweetener comprises one or more of sucralose, xylitol, aspartame, acesulfame potassium, acesulfame salts, steviol glycosides (e.g., Stevia®, Truvia®), thaumatin (e.g., Talin®), glycyrrhizic acid salts (MagnaSweet®), or combinations thereof. In one aspect, the sweetener comprises sucralose.

In another embodiment described herein, the soft capsule shell comprises one or more polymer modifiers. In one embodiment, the polymer modifier comprises an organic acid. In another embodiment, the polymer modifiers comprise one or more of citric acid, acetic acid, lactic acid, malic acid, tartaric acid, glutamic acid, aspartic acid, malic acid, succinic acid, fumaric acid, or combinations thereof. In one aspect, the polymer modifier comprises citric acid.

In another embodiment, the soft capsule shell comprises one or more solvents. In one aspect, the solvent comprises water.

In one embodiment, the one or more polymer comprises a weight percentage of about 20% to about 60% by weight of the shell, including each integer within the specified range. In another embodiment, the one or more polymers comprise about 20% to about 50%, about 25% to about 55%, or about 30% to about 45% by weight of the shell. In one aspect, the total polymer comprises about 20%, about 25%, about 30%, about 35%, about 40%, about 45%, about 50%, about 55%, or about 60% by weight of the shell. In another aspect, the total one or more polymers comprise about 32% by weight of the shell. In another aspect, the total one or more polymers comprise about 30%, about 31%, about 33%, 34%, or about 37% by weight of the shell.

In another embodiment, the one or more polymers comprise gelatin having a Bloom of about 150 and a weight percentage of about 10% to about 40% by weight of the shell, including each integer within the specified range. In one embodiment, gelatin having a Bloom of about 150 comprises about 10% to about 30%, about 15% to about 30%, about 15% to about 25%, or about 15% to about 20% by weight of the shell. In one aspect, gelatin having a Bloom of about 150 comprises about 10%, about 15%, about 20%, about 25%, about 30%, about 35%, or about 40% by weight of the shell. In another aspect, gelatin having a Bloom of about 150 comprises about 19% by weight of the shell. In another aspect, gelatin having a Bloom of about 150 comprises about 14%, about 16%, about 18%, about 20%, or about 22% by weight of the shell.

In another embodiment, the one or more polymers comprise a gelatin having a Bloom of about 100 and a weight percentage of about 1% to about 30% by weight of the shell, including each integer within the specified range. In another embodiment, gelatin having a Bloom of about 100 comprises about 1% to about 20%, 1% to about 15%, about 1% to about 10%, or about 5% to about 10% by weight of the shell. In one aspect, gelatin having a Bloom of about 100 comprises about 1%, about 5%, about 10%, about 15%, about 20%, about 25% or about 30% by weight of the shell. In another aspect, gelatin having a Bloom of about 100 comprises 8% by weight of the shell. In another aspect, gelatin having a Bloom of about 100 comprises about 5%, about 7%, about 10%, 15%, 18%, or about 28% by weight of the shell.

In another embodiment, the one or more polymers comprise gelatin hydrolysate having a weight percentage of about 0 to about 7% by weight of the shell, including each integer within the specified range. In one embodiment, gelatin hydrolysate comprises about 0.25% to about 6.75%, about 0.50% to about 6.50%, about 1% to about 6%, or about 1.5% to about 5.5% by weight of the shell. In one aspect, gelatin hydrolysate comprises about 0%, about 2%, about 4%, or about 7% by weight of the shell. In another aspect, the gelatin hydrolysate comprises about 5% by weight of the shell. In another aspect, the gelatin hydrolysate comprises about 2%, about 4%, about 4.5%, about 5.5%, or about 6% by weight of the shell.

In another embodiment, the one or more polymers comprise hydrolyzed collagen at a weight percentage of about 0% to about 7% by weight of the shell, including each integer within the specified range. In one embodiment, hydrolyzed collagen comprises about 0.25% to about 6.75%, about 0.50% to about 6.50%, about 1% to about 6%, or about 1.5% to about 5.5% by weight of the shell. In one aspect, hydrolyzed collagen comprises about 0%, about 2%, about 4%, or about 7% by weight of the shell. In another aspect, hydrolyzed collagen comprises about 5% by weight of the shell. In another aspect, hydrolyzed collagen comprises about 4%, about 4.5%, about 5%, about 5.5%, or about 6% by weight of the shell.

In another embodiment, one or more plasticizers comprise a weight percentage of about 30% to about 70% by weight of the shell, including each integer within the specified range. In one embodiment, the one or more plasticizers comprise about 30% to about 60%, about 30% to about 50%, or about 35% to about 45% by weight of the shell. In one aspect, one or more plasticizers comprise about 30%, about 35%, about 40%, about 45%, about 50%, about 55%, about 60%, about 65%, or about 70% by weight of the shell. In another aspect, the total plasticizer comprises about 43% by weight of the shell. In another aspect, the total plasticizer comprises about 36%, about 39%, about 40%, about 41%, about 42%, about 44%, or about 45% by weight of the shell.

In another embodiment, the one or more plasticizers comprise glycerol, xylitol, maltitol, or a combination thereof and comprise a weight percentage of about 10% to about 50% by weight of the shell, including each integer within the specified range. In another embodiment, glycerol comprises about 10% to about 40%, about 15% to about 35%, about 15% to about 30%, or about 20% to about 25% by weight of the shell. In one aspect, glycerol comprises about 10%, about 15%, about 20%, about 25%, about 30%, about 35%, about 40%, about 45%, or about 50% by weight of the shell. In another aspect, glycerol comprises about 24% by weight of the shell. In another aspect, glycerol comprises about 19%, about 20%, about 21%, about 22%, about 23%, about 24%, or about 25% by weight of the shell.

In another embodiment, the one or more plasticizers comprise xylitol having a weight percentage of 0% to about 20% by weight of the shell, including each integer within the specified range. In one embodiment, xylitol comprises about 1% to about 15%, about 1% to about 10%, or about 1% to about 5% by weight of the shell. In one aspect, xylitol comprises about 0%, about 5%, about 10%, about 15%, or about 20% by weight of the shell. In another aspect, xylitol comprises about 3% by weight of the shell. In another aspect, xylitol comprises about 0.5%, about 1%, about 4%, or about 5% by weight of the shell.

In another embodiment, the one or more plasticizers comprise maltitol having a weight percentage of about 1% to about 30% by weight of the shell, including each integer within the specified range. In one embodiment, maltitol comprises about 1% to about 30%, about 5% to about 25%, about 10% to about 25%, or about 15% to about 20% by weight of the shell. In one aspect, maltitol comprises about 1%, about 5%, about 10%, about 15%, about 20%, about 25%, or about 30% by weight of the shell. In another aspect, maltitol comprises about 17% by weight of the shell. In another aspect, maltitol comprises about 15%, about 16%, or about 18% by weight of the shell.

In another embodiment, the one or more polymer modifiers comprise about 0.01% to about 2% by weight of the shell, including each integer within the specified range. In one embodiment, the one or more polymer modifiers comprise about 0.25% to about 1.5%, about 0.25% to about 1%, or about 0.25% to about 0.75% by weight of the shell. In one aspect, the polymer modifier comprises about 0%, about 0.25%, about 0.50%, about 0.75%, about 1%, about 1.25%, about 1.50%, about 1.75%, or about 2.0% by weight of the shell. In another aspect, the polymer modifier comprises about 0.5% by weight of the shell. In another aspect, the polymer modifier comprises about 0.25%, about 0.3%, or about 0.6% by weight of the shell.

In another embodiment, the polymer modifier comprises citrate having a weight percentage of about 0.01% to about 2% by weight of the shell, including each integer within the specified range. In another embodiment, citrate comprises about 0.25% to about 1.5%, about 0.25% to about 1%, or about 0.25% or about 0.75% by weight of the shell. In one aspect, citrate comprises about 0%, about 0.25%, about 0.50%, about 0.75%, about 1%, about 1.25%, about 1.50%, about 1.75%, or about 2.0% by weight of the shell. In another aspect, citrate comprises about 0.5% by weight of the shell. In another aspect, citrate comprises about 0.25%, about 0.3%, or about 0.6% by weight of the shell.

In another embodiment, the one or more sweeteners comprise sucralose having a weight percentage of about 0.01% to about 5% by weight of the shell, including each integer within the specified range. In one embodiment, sucralose comprises about 0.1% to about 0.9%, about 0.1% to about 0.75%, or about 0.1% to about 0.5% by weight of the shell. In one aspect, sucralose comprises about 0%; about 0.25%, about 0.50%, about 0.75%, or about 1% by weight of the shell. In another aspect, sucralose comprises about 0.2%. In another aspect, sucralose comprises about 0.1%, about 0.15%, about 0.25%, or about 0.3% by weight of the shell.

In another embodiment, the one or more sweeteners comprise xylitol having a weight percentage of about 0.01% to about 5% by weight of the shell, including each integer within the specified range. In one embodiment, xylitol comprises about 0.1% to about 4%, about 0.1% to about 3%, or about 0.5% to about 2.5% by weight of the shell. In one aspect, xylitol comprises about 0%; about 0.25%, about 0.50%, about 0.75%, about 1%, about 1.5%, about 2%, or about 2.5% by weight of the shell. In another aspect, xylitol comprises about 2.5%. In another aspect, xylitol comprises about 1.5%, about 2%, about 2.25%, or about 2.75% by weight of the shell.

In another embodiment, one or more solvents comprise about 10% to about 40% by weight of the shell, including each integer within the specified range. In another embodiment, the solvents comprise about 10% to about 35%, about 15% to about 30%, or about 20% to about 30% by weight of the shell. In another aspect, the solvents comprise about 10%, about 15%, about 20%, about 25%, about 30%, about 35%, or about 40% by weight of the shell. In another aspect, the solvents comprise 23% by weight of the shell. In another aspect, the solvents comprise about 17%, about 20%, about 25%, or about 30% by weight of the shell.

In another embodiment, the solvent comprises water having a weight percentage of about 10% to about 40% by weight of the shell, including each integer within the specified range. In another embodiment, water comprises about 10% to about 35%, about 15% to about 30%, or about 20% or about 30% by weight of the shell. In another aspect, water comprises about 10%; about 15%, about 20%, about 25%, about 30%, about 35%, or about 40% by weight of the shell. In another aspect, water comprises 23% by weight of the shell. In another aspect, water comprises about 17%, about 20%, about 25%, or about 30% by weight of the shell.

In another embodiment, the ratio of total polymer to total plasticizer in the shell comprises about 1:1 to about 1:2, including each ratio within the specified range. In another embodiment, the ratio of total polymer to total plasticizer in the shell is about 1:1 to about 1:1.8, about 1:1 to about 1:1.6, about 1:1 to about 1:4. In one aspect, the ratio of total polymer to total plasticizer in the shell is about 1:1.1, about 1:1.2, about 1:1.3, about 1:1.4, about 1:1.5, about 1:1.6, about 1:1.7, about 1:1.8, about 1:1.9, or about 1:2. In another aspect, the ratio of total polymer to total plasticizer in the shell is about 1:1.3. In another aspect, the ratio of total polymer to total modifier in the shell is about 1:0.75, about 1:1.25, about 1:1.5, or about 1:1.75.

In another embodiment, the ratio of total polymer to total polymer modifier in the shell comprises about 1:0.01 to about 1:0.1, including each ratio within the specified range. In one embodiment, the ratio of total polymer to total polymer modifier in the shell is about 1:0.01 to about 1:0.08, about 1:0.01 to about 1:0.06, or about 1:0.01 to about 1.04.

In one aspect, the ratio of total polymer to total plasticizer in the shell is about 1:0.01, about 1:0.02, about 1:0.03, about 1:0.04, about 1:0.05, about 1:0.06, about 1:0.07, about 1:0.08, about 1:0.09, or about 1:1. In another aspect, the ratio of total polymer to total polymer modifier in the shell is about 1:0.02. In another aspect, the ratio of total polymer to total modifier in the shell is about 1:0.01, or about 1:0.03.

In one embodiment, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical compositions as described herein. The process includes preparing a gel mass composition comprising one or more polymers, one or more plasticizers, one or more polymer modifiers, one or more solvents, and appropriate flavorings, sweeteners, coloring agents, or other excipients; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In one embodiment, the hydrophilic vehicle may be anhydrous and compatible with soft gelatin capsules. Non-limiting exemplary vehicles comprise Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F. 68, Maisine™ 35-1, mannitol, Miglyol® 812, Pearlitol® Flash, Peceol®, Plurol® Oleique CC 497, Povidone K 17, Povidone K 30, polyethylene glycol 200, polyethylene glycol 400, polyethylene glycol 600, polyethylene glycol 800, polyethylene glycol 1000, polyethylene glycol 2000, polyethylene glycol 3350, propylene glycol, glycerol, Lycasin 80/55, sorbitol special, xylitol, maltitol or mixtures thereof. In on embodiment the hydrophilic vehicle comprises one or more hydro-alcohols including polyethylene glycols of a molecular weight ranging from about 200 to about 8000, or a mixture or combination thereof.

In another embodiment, the hydrophilic vehicle may comprise a hygroscopic polymer. In one embodiment, the hygroscopic polymers include polyvinylpyrrolidone, copovidone, hydroxypropylmethylcellulose, hydroxypropylcellulose, ethyl cellulose, methylcellulose, and polyethylene oxide. Suitable hygroscopic polymers include polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, such as POLYOX™ 100,000-600,000 MW, acacia, dextrin, cyclodextrins, starch, poly hydroxyethylmethacrylate, a water-soluble non-ionic polymethacrylate or copolymer thereof, a modified cellulose, a modified polysaccharide, a non-ionic gum, or a non-ionic polysaccharide.

In another embodiment, the hydrophilic vehicle may comprise one or more lipids or lipophilic vehicles. In one aspect, the lipid or lipophilic vehicle may be a liquid or a solid or a semisolid lipid or lipophilic vehicle. Suitable non-limiting liquid lipid or lipophilic vehicles comprise olive oil, soybean oil, sunflower oil, canola oil, palmitoleic acid, oleic acid, myristoleic acid, linoleic acid, arachidonic acid, paraffin oil, mineral oil, or a mixture or combination thereof. The lipid or lipophilic vehicle can be a semi-solid lipophilic vehicle such as a polyethylene glycol glyceride ester, e.g., Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02; a paraffin wax, carnauba wax, or bee's wax.

In another embodiment, the hydrophilic vehicle may comprise release regulators such as fatty acid salts, fatty acid esters, or fatty acid polyoxyethylene derivatives. The release regulator can also be a surfactant having a hydrophilic/lipophilic balance (HLB) value between about 2 and about 40. The HLB characteristic of surfactants can be determined in accordance with "*Physical Pharmacy: Physical Chemical Principles in the Pharmaceutical Sciences*," Fourth Edition, pp. 371-373, A. Martin, Ed., Lippincott Williams & Wilkins, Philadelphia (1993), which is incorporated by reference herein for such teachings.

In another embodiment, the hydrophilic vehicle may comprise emulsifying or solubilizing agents such as acacia, cholesterol, diethanolamine, glyceryl monostearate, lanolin alcohols, lecithin, mono- and di-glycerides, monoethanolamines, oleic acids, oleyl alcohols, poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, simethicone, trolamine, emulsifying wax, or combinations thereof.

In one embodiment described herein, the matrix fill comprises one or more hydrophilic vehicles. In another aspect, the one or more hydrophilic vehicles comprise propylene glycol, polyethylene glycol 400, polyvinylpyrrolidone K30, or combinations thereof.

In another embodiment described herein, the matrix fill comprises one or more flavorings. In one embodiment, the one or more flavorings comprise citric acid, lactic acid, sodium citrate, anethole, benzaldehyde, ethyl vanillin, Eucalyptol, glycine, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin or combinations thereof. In one aspect, the flavorings comprise one or more of citric acid, acetic acid, lactic acid, malic acid, tartaric acid, or combinations thereof. In another aspect, the flavorings comprise citric acid, lactic acid, or combinations thereof.

In another embodiment, the matrix fill comprises at least one or more sweeteners. In one embodiment, the one or more sweeteners comprise mannitol, thaumatin, glycyrrhizic acid salt, maltitol, sucralose, acesulfame salts, steviol glycosides (e.g., Stevia®, Truvia®), saccharin, calcium saccharin, sodium saccharin, aspartame, acesulfame potassium, agave nectar, high-fructose corn syrup, honey, dextrates, dextrose, excipient dextrose and simple sugars such as glucose, fructose, sucrose, sucralose, lactose, or combinations thereof. In one aspect, the sweeteners comprise one or more of mannitol, maltitol (e.g., Lycasin®), xylitol, sucralose, thaumatin (e.g., Talin®), glycyrrhizic acid salts (MagnaSweet®), or combinations thereof.

In another embodiment the matrix fill comprises at least one solvent. In one aspect, the solvent is water.

Additional pharmaceutical excipients useful for capsule shells or matrix fills as described herein include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); Colorants (caramel, red, yellow, black or blends; ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, mono- and di-glycerides, monoethanolamine (adjunct), lecithin, oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerol, hexylene glycol, sorbitol); Plasticizers (e.g., castor oil, diacetylated monoglycerides, diethyl phthalate, glycerol, mono- and di-acetylated monoglycerides, propylene glycol, triacetin, triethyl citrate); Polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Surfactants (simethicone); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); Thickening agents (gelatin having a Bloom strength of 50-100); Tonicity agent (dextrose, glycerol, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyl dodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

In one embodiment, one or more hydrophilic vehicles comprise about 20% to about 95% by weight of the matrix fill, including each integer within the specified range. In another embodiment, the one or more hydrophilic vehicles comprise about 20% to about 50%, about 25% to about 50%, about 30% or about 45%, about 40% to about 60%, or about 50% to about 95% by weight of the matrix fill. In one aspect, the total hydrophilic vehicle comprises about 20%, about 25%, about 30%, about 35%, about 40%, about 45%, about 50%, about 55%, about 60%, about 65%, about 70%, about 75%, about 80%, about 85%, or about 90% by weight of the matrix fill. In another aspect, the total hydrophilic vehicle comprises about 40%, about 60%, about or about 90% by weight of the matrix fill.

In another embodiment, the hydrophilic vehicle comprises polypropylene glycol having a weight percentage of about 0% to about 20% by weight of the matrix fill, including each integer within the specified range. In one embodiment, the polypropylene glycol comprises about 0% to about 15%, about 0% to about 10%, or about 5% to about 10% by weight of the matrix fill. In one aspect, the polypropylene glycol comprises about 0%, about 5%, about 10%, about 15%, or about 20% by weight of the matrix fill. In another aspect, polypropylene glycol comprises about 8% by weight of the shell. In another aspect, the polypropylene glycol comprises about 2%, about 6%, about 7%, or about 9% by weight of the fill.

In another embodiment, the hydrophilic vehicle comprises polyethylene glycol 400 having a weight percentage of about 0.01% to about 50% by weight of the matrix fill, including each integer within the specified range. In one embodiment, polyethylene glycol 400 comprises about 0.01% to about 40%, about 0.1% to about 30%, or about 10% to about 30% by weight of the matrix fill. In one aspect, polyethylene glycol 400 comprises about 1%, about 10%, about 15%, about 20%, about 25%, about 30%, about 40%, about 45%, or about 50% by weight of the matrix fill. In another aspect, polyethylene glycol 400 comprises about 20% by weight of the fill. In another aspect, polyethylene glycol 400 is about 1%, about 16%, about 18%, about 20%, about 25%, about 30%, about 45%, or about 50% by weight of the fill.

In another embodiment, the hydrophilic vehicle comprises polyvinylpyrrolidone K30 having a weight percentage of about 0% to about 2% by weight of the matrix fill, including each integer within the specified range. In one embodiment, polyvinylpyrrolidone K30 comprises about 0.25% to about 1.75%, about 0.50% to about 1.75%, or about 0.75% to about 1.75% by weight of the matrix fill. In one aspect, polyvinylpyrrolidone K30 comprises about 0%, about 0.25%, about 0.50%, about 0.75%, about 1%, about 1.25%, about 1.5%, about 1.75%, or about 2% by weight of the matrix fill. In another aspect, polyvinylpyrrolidone K30 comprises about 1.2% by weight of the fill. In another aspect, polyvinylpyrrolidone K30 comprises about 1%, about 1.1%, about 1.3%, about 1.4%, about 1.5%, or about 1.7% by weight of the fill.

In another embodiment, one or more excipients comprise about 0.1% to about 25% by weight of the matrix fill, including each integer within the specified range. In one embodiment, the one or more excipients comprise about 0.1% to about 10%, about 10% to about 25%, or about 5% to about 15% by weight of matrix fill. In one aspect, the one or more excipients comprise about 0.1%, 1%, about 5%, about 10%, about 15%, about 20%, or about 25%, by weight of the matrix fill. In one aspect, the one or more excipients comprise about 10% by weight of the fill. In another aspect, the one or more excipients comprise about 1%, about 2%, about 2.5%, about 3%, about 4%, about 5%, about 10%, about 15%, or about 20% by weight of the fill.

In another embodiment, one or more sweeteners comprise about 0.1% to about 20% by weight of the matrix fill, including each integer within the specified range. In one embodiment, the one or more sweeteners comprises about 0.1% to about 15%, about 0.1% to about 10%, or about 0.1% to about 5% by weight of the matrix fill. In one aspect, the one or more sweeteners comprises about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% by weight of the matrix fill. In one aspect, the one or more sweeteners comprises about 1%, about 2%, about 3%, about 4%, about 5%, about 6%, about 7%, about 8%, about 9%, about 10%, about 12%, or about 15% by weight of the matrix fill. In one aspect, the one or more sweeteners comprise about 0.5% by weight of the matrix fill. In another aspect, the one or more sweeteners comprise about 0.2%, about 0.3%, about 0.4%, or about 0.7% by weight of the fill.

In another embodiment, the one or more sweeteners comprise sucralose having a weight percentage of about 0% to about 2% by weight of the matrix fill, including each integer within the specified range. In another embodiment, sucralose comprises about 0.1% to about 1.74%, about 0.2% to about 1.5%, about 0.3% to about 1.5%, or about 0.4% to about 1% by weight of the matrix fill. In one aspect, sucralose comprises about 0%, about 0.25%, about 0.5%, about 0.75%, about 1%, about 1.25%, about 1.5%; about 1.75%, or about 2% by weight of the matrix fill. In another aspect, sucralose comprises about 0.6% by weight of the fill. In another aspect, sucralose comprises about 0.5%, about 0.55%, or about 0.65% by weight of the fill.

In one embodiment, the sweeteners comprise mannitol having a weight percentage of about 0% to about 5% by weight of the matrix fill, including each integer within the specified range. In one embodiment, mannitol comprises about 0.1% to about 4%, about 0.2% to about 3%, or about 0.3% to about 2% by weight of the matrix fill. In one aspect, mannitol comprises about 0%, about 1%, about 2%, about 3%, about 4%, or about 5% by weight of the matrix fill. In another aspect, mannitol comprises about 0.5% by weight of the fill. In another aspect, mannitol comprises about 0.3%, about 0.6%, or about 0.9% by weight of the fill.

In another embodiment, the sweeteners comprise thaumatin at a weight percentage of about 0% to about 5% by weight of the matrix fill, including each integer within the specified range. In one embodiment, thaumatin comprises about 0.1% to about 4%, about 0.2% to about 3%, or about 0.3% to about 2% by weight of the matrix fill. In one aspect, thaumatin comprises about 0%, about 1%, about 2%, about 3%, about 4%, or about 5% by weight of the matrix fill. In another aspect, thaumatin comprises about 0.5% by weight of the fill. In another aspect, thaumatin comprises about 0.3%, about 0.6%, or about 0.9% by weight of the fill.

In another embodiment, the sweeteners comprise acesulfame potassium at a weight percentage of about 0% to about 5% by weight of the matrix fill, including each integer within the specified range. In one embodiment, acesulfame potassium comprises about 0.1% to about 4%, about 0.2% to about 3%, or about 0.3% to about 2% by weight of the matrix fill. In one aspect, acesulfame potassium comprises about 0%, about 1%, about 2%, about 3%, about 4%, or about 5% by weight of the matrix fill. In another aspect, acesulfame potassium comprises about 0.6% by weight of the fill. In another aspect, acesulfame potassium comprises about 0.3%, about 0.5%, or about 0.9% by weight of the fill.

In another embodiment, the sweeteners comprise a glycyrrhizic acid salt having a weight percentage of about 0% to about 5% by weight of the matrix fill, including each integer within the specified range. In one embodiment, the glycyrrhizic acid salt comprises about 0.1% to about 4%, about 0.2% to about 3%, or about 0.3% to about 2% by weight of the matrix fill. In one aspect, the glycyrrhizic acid salt comprises about 0%, about 1%, about 2%, about 3%, about 4%, or about 5% by weight of the matrix fill. In another aspect, the glycyrrhizic acid salt comprises about 0.5% by weight of the fill. In another aspect, the glycyrrhizic acid salt comprises about 0.3%, about 0.6%, or about 0.9% by weight of the fill.

In one embodiment, one or more flavorings comprise about 0.1% to about 5% by weight of the matrix fill, including each integer within the specified range. In another embodiment, the one or more flavorings comprise about 0.1% to about 4.5%, about 0.1% to about 3.5%, or about 0.1% to about 3% by weight of the matrix fill. In one aspect, the flavorings comprise about 0.01, about 1%, about 1.5%, about 1.6%, about 2.0%, about 2.5%, about 3%, about 3.5%, about 4%, about 4.5%, about 5%, about 5.5%, or about 6% by weight of the matrix fill. In another aspect, the flavorings comprise about 4% by weight of the fill. In another aspect, the flavorings comprise about 0.01%, about 0.09%, about 1%, about %, or about 5% by weight of the fill.

In another embodiment, the flavorings comprise citric acid having a weight percentage of about 0.01% to about 3% by weight of the matrix fill, including each integer within the specified range. In one embodiment, citric acid comprises about 0.25% to about 2.75%, about 0.5% to about 2.5%, or about 0.75% to about 2.25% by weight of the matrix fill. In one aspect, citric acid comprises about 0%, about 0.5%, about 1%, about 1.5%, about 2%, about 2.5%, or about 3% by weight of the matrix fill. In another aspect, citric acid comprises about 1% by weight of the fill. In another aspect, citric acid comprises about 0.5%, about 0.75%, about 1.25%, or about 1.5% by weight of the fill.

In another embodiment, the flavorings comprise lactic acid having a weight percentage of about 0% to about 3% by weight of the matrix fill, including each integer within the specified range. In one embodiment, lactic acid comprises about 0.25% to about 2.75%, about 0.5% to about 2.5%, or about 0.75% to about 2.25% by weight of the matrix fill. In one aspect, lactic acid comprises about 0%, about 0.5%, about 1%, about 1.5%, about 2%, about 2.5%, or about 3% by weight of the matrix fill. In another aspect, lactic acid comprises about 1% by weight of the fill. In another aspect, lactic acid comprises about 0.5%, about 0.75%, about 1.25%, or about 1.5% by weight of the fill.

In one embodiment, the flavorings comprise sodium citrate having a weight percentage of about 0% to about 3% by weight of the matrix fill, including each integer within the specified range. In another embodiment, sodium citrate comprises about 0.25% to about 2.75%, about 0.5% to about 2.5%, or about 0.75% to about 2.25% by weight of the matrix fill. In one aspect, sodium citrate comprises about 0%, about 0.5%, about 1%, about 1.5%, about 2%, about 2.5%, or about 3% by weight of the matrix fill. In another aspect, sodium citrate comprises about 1% by weight of the fill. In another aspect, sodium citrate comprises about 0.5%; about 0.75%, about 1.25%, or about 1.5% by weight of the fill.

In another embodiment, a solvent comprises about 0% to about 15% by weight of the matrix fill, including each integer within the specified range. In another embodiment, the solvent comprises about 0.5% to about 13%, about 1% to about 11%, about 1.5% to about 9%, or about 2% to about 6% by weight of the matrix fill. In another aspect, the solvent comprises about 0%, about 5%, about 10%, or about 15% by weight of the matrix fill. In another aspect, the solvent comprises about 5.5% by weight of the matrix fill. In another aspect, the solvent comprises about 4.5%, about 5%, about 6%, or about 6.5% by weight of the matrix fill.

In another embodiment, the solvent comprises water at a weight percentage of about 0% to about 15% by weight of the matrix fill, including each integer within the specified range. In one embodiment, water comprises about 0.5% to about 13%, about 1% to about 11%, about 1.5% to about 9%, or about 2% to about 6% by weight of the matrix fill. In another aspect, water comprises about 0%, about 5%, about 10%, or about 15% by weight of the matrix fill. In another aspect, water comprises 5.5% by weight of the matrix fill. In another aspect, water comprises about 4.5%, about 5%, about 6%, or about 6.5% by weight of the matrix fill.

In another embodiment, the shell comprises one or more colorings. Typical food colorings such as FD&C food dyes or D&C dyes can be used in any combinations to create the desired color. Dyes can be used in weight percentages from 0.0001% to 0.5%, including all integers and fractions within the specified ranges.

In one embodiment described herein, the compositions described herein comprise one or more active pharmaceutical ingredients. In one embodiment, one active pharmaceutical ingredient is the only active ingredient in the pharmaceutical composition. In another embodiment, one or more active pharmaceutical ingredients or drugs are included in the pharmaceutical composition. In another embodiment, the active pharmaceutical ingredient can be an active pharmaceutical ingredient, a derivative thereof, or combinations thereof.

In one embodiment, the compositions described herein comprise one or more active pharmaceutical ingredients useful for treating, retarding the progression of, delaying the onset of, prophylaxis of, amelioration of, or reducing the symptoms of pain, inflammation, fever, or symptoms stemming from cough or cold. In one embodiment described herein, the active pharmaceutical ingredient comprises one or more of astemizole, azelastine, azatadine, brompheniramine, carbinoxamine, cetirizine, chlorpheniramine, clemastine, cyproheptadine, desloratadine, dexbrompheniramine, dexchlorpheniramine, diphenhydramine, fexofenadine, hydroxyzine, levocetirizine, loratadine, phenindamine, pheniramine, phenyltoloxamine, promethazine, pyrilamine, terfenadine, tripelennamine, triprolidine, acetyl dihydrocodeine, benproperine, benzonatate, benzylmorphine, bibenzonium bromide, butamirate, butorphanol, carbetapentane, chlophedianol, clobutinol, clofedanol, cloperastine, codeine, dextromethorphan, diacetylmorphine, dibunate, dihydrocodeine, dimemorfan, dimethoxanate, diphenhydramine, dropropizine, droxypropine, ethylmorphine, fedrilate, glaucine, hydrocodone, hydromorphone, isoaminile, laudanum, levodropropizine, levomethadone, levopropoxyphene, meprotixol, methadone, morclofone, nepinalone, nicocodine, nicodicodine, normethadone, noscapine, oxeladin, oxolamine, pentoxyverine, pholcodine, pipazetate, pipleridione, prenoxdiazine, tipepidine, zipeprol, acetylcysteine, althea root, ambroxol, antimony pentasulfide, bromhexine, carbocisteine, cineole, combinations, combinations, creosote, dembrexine hydrochloride, domiodol, dornase alfa, eprazinone, erdosteine, guaiacolsulfonate, guaifenesin, hederae helicis folium, ipecacuanha, letosteine, levo verbenone, mannitol, mesna, neltenexine, potassium iodide, senega, sobrerol, stepronin, tiopronin, tyloxapol, or combinations thereof. In one aspect, the active pharmaceutical ingredient comprises one or more of dextromethorphan hydrobromide, menthol, or combinations thereof.

In one embodiment described herein, the active pharmaceutical ingredient is an anti-allergy agent. Exemplary anti-allergy agents include pseudoephedrine, cetirizine, loratadine, fexofenadine, diphenhydramine, levocetirizine, desloratadine, or combinations thereof.

In one embodiment described herein, the active pharmaceutical ingredient is an oral rinsing agent. Exemplary oral rinsing agents include phenol, ethanol, thymol, eucalyptol, ethanol, methyl salicylate, chlorhexidine gluconate, cetylpyridinium chloride, hexetidine, triclosan, hydrogen peroxide, domiphen bromide, or combinations thereof. In one embodiment described herein, the active pharmaceutical ingredient comprises an oral rinsing agent comprising one or more of ethanol (about 20% to about 30%) menthol (0.042%), thymol (0.064%), methyl salicylate (0.06%), and eucalyptol (0.092%).

In one embodiment described herein, the active pharmaceutical ingredient is an antidiarrheal or antacid comprising bismuth subsalicylate, loperamide hydrochloride, aluminum hydroxide, magnesium hydroxide, simethicone, aluminum carbonate, calcium carbonate, sodium bicarbonate, magnesium aluminum silicate, hydrotalcite, magaldrate, cimetidine, famotidine, nizatidine, ranitidine, lansoprazole, omeprazole, esomeprazole, rabeprazole, pantoprazole, dexlansoprazole, or combinations thereof. In one embodiment described herein, the active pharmaceutical ingredient comprises one or more of bismuth subsalicylate (~17.6 mg), benzoic acid, D&C Red No. 22, D&C Red No. 28, flavoring, magnesium aluminum silicate, methylcellulose, sodium saccharin, salicylic acid, sodium salicylate, sorbic acid, and water.

In another embodiment, the active pharmaceutical ingredient is an irritable bowel syndrome therapeutic. Exemplary non-limiting active pharmaceutical ingredients useful for the treatment of irritable bowel syndrome comprise antidiarrheals such as atropine, diphenoxylate (Lomotil®), dicyclomine (Bentyl®), loperamide (Imodium®), rifaximin (Xifaxan®), alosetron (Lotronex®); bile acid binding agents such as cholestyramine (Prevailite®); constipation therapeutics such as linaclotide (Linzess®) or lubiprostone (Amitiza) or combinations thereof.

In one embodiment described herein, the active pharmaceutical ingredient is a constipation therapeutic such as linaclotide (Linzess®) or lubiprostone (Amitiza®), methylcellulose, polycarbophil, psyllium, mineral oil, glycerol, docusate sodium, sodium bicarbonate, sodium phosphate, magnesium citrate, magnesium oxide, magnesium sulfate, bisacodyl, sennosides, senna, castor oil or combinations thereof.

In another embodiment described herein, the active pharmaceutical ingredient comprises one or more corticosteroids for treating inflammatory diseases and conditions and inflammation of the gastrointestinal tract, including but not limited to esophageal inflammation. In one embodiment described herein, the active pharmaceutical ingredient comprises one or more corticosteroids including but not limited to alclometasone, amcinonide, beclometasone, betamethasone, budesonide, ciclesonide, clobetasol, clobetasone, clocortolone, cloprednol, cortivazol, deflazacort, deoxycorticosterone, desonide desoximetasone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluticasone, fluticasone propionate, fluprednidene, formocortal, halcinonide, halometasone, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone, prednisolone, prednylidene, rimexolone, tixocortol, triamcinolone, ulobetasol, combinations thereof, or pharmaceutically acceptable salts, or esters thereof.

In another embodiment described herein, the active pharmaceutical ingredient comprises one or more of 5-fluorouracil, 5-fluorodeoxyuridine, capecitabine, derivatives thereof, or combinations thereof for treating neoplasia, including but not limited to head and neck neoplasia.

In another embodiment described herein, the active pharmaceutical ingredient comprises one or more of calcium supplements or calcimimetics including but not limited to cinacalcet, derivatives thereof, or combinations thereof for treating hyperthyroidism, hypercalcemia, hyperparathyroidism, parathyroid carcinoma, or a combination thereof.

In some embodiments, the active pharmaceutical ingredient is a sleep aid. Examples of sleep aids include, but are not limited to doxylamine, diphenhydramine hydrochloride, melatonin, 1-theanine, or combinations thereof.

In some embodiments, the active pharmaceutical ingredient is an oral saliva substitute, such as, for example: monofluorophosphate, lactoferrin, lysozyme, lactoperoxidase, glucose oxidase, mutanase, dextranase, glycerol, or combinations thereof.

In some embodiments, the active pharmaceutical ingredient is a teeth-bleaching or teeth-whitening agent, including but not limited to carbamide peroxide, sodium bicarbonate, hydrated silica, silicon dioxide, polyvinylpyrrolidone, potassium nitrate, sodium monofluorophosphate, sodium tripolyphosphate, strontium chloride, or combinations thereof.

In another embodiment, the active pharmaceutical ingredient is a tooth enamel-enhancing agent. Exemplary tooth enamel enhancing agents include potassium nitrate, strontium acetate, strontium chloride, calcium sodium phosphosilicate, or combinations thereof.

In another embodiment, the active pharmaceutical ingredient is an oral anesthetic, including but not limited to benzocaine, lidocaine, clove oil, or combinations thereof.

In one embodiment, the active pharmaceutical ingredient is an effervescent including but not limited to sodium bicarbonate, citric acid, tartaric acid, or combinations thereof. Effervescent may be combined with one or more cold, cough, allergy, nasal decongestant, antitussive, expectorant, antihistamine, stimulant, sedative, anti-inflammatory, antibiotic, anti-viral, anti-asthmatic, anti-migraine, hypnotic, narcotic analgesic, or narcotic antagonist active pharmaceutical ingredients, or further combinations thereof.

In one embodiment described herein, the active pharmaceutical ingredient is one or more non-steroidal anti-inflammatory drugs (NSAID). Non-limiting examples of NSAID active pharmaceutical ingredients comprise aspirin, ibuprofen, aceclofenac, acemetacin, aloxiprin, azapropazone, benorilate, bromfenac, carprofen, celecoxib, choline magnesium salicylate, diclofenac, diflunisal, etodolac, etoricoxib, fisalamine, fenbufen, fenoprofen, flurbiprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, paracetamol, parecoxib, phenylbutazone, piroxicam, salicyl salicylate, sulindac, sulfinpyrazone, suprofen, tenoxicam, tiaprofenic acid, tolmetin, valdecoxib, or combinations thereof.

In another embodiment, suitable active pharmaceutical ingredients can comprise analgesics, such as, for example: acetylsalicylic acid, aloxiprin, aminophenazone, anilides, benorilate, benzomorphan derivatives, bezitramide, bucetin, buprenorphine, butorphanol, carbasalate calcium, choline salicylate, codeine, dextromoramide, dextropropoxyphene, dezocine, diamorphine, diflunisal, dihydrocodeine, dihydrocodone, dihydromorphine, diphenylpropylamine derivatives, dipyrocetyl, ethenzamide, fentanyl, floctafenine, flupirtine, glafenine, guacetisal, hydrocodone, hydrocodone bitartrate, hydromorphone, hydromorphone hydrochloride, imidazole salicylate, ketobemidone, metamizole sodium, methadone, morphinan derivatives, morphine, morphine sulphate pentahydrate, morphine-6-glucuronode, morpholine salicylate, nalbuphine, natural opium alkaloids, nefopam, nicomorphine, nifenazone, norhydrocodone, noroxycodone, opioids, opium, oripavine derivatives, oxycodeine, oxycodone, oxycodone hydrochloride, oxymorphone, papaveretum, pentazocine, pethidine, phenacetin, phenazocine, phenazone, phenylpiperidine derivatives, piritramide, potassium salicylate, propacetamol, propyphenazone, pyrazolones, rimazolium, salicylamide, salicylic acid derivatives, salsalate, sodium salicylate, tapentadol, tilidine, tramadol, viminol, ziconotide, or combinations thereof.

In another embodiment, the active pharmaceutical ingredient disclosed herein includes an opioid, the opioid is selected from buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, dihydromorphine, or combinations thereof.

In one embodiment described herein, the active pharmaceutical ingredient is a probiotic. Exemplary probiotics include *Bifidobacterium infantis* 35624, *Bifidobacterium lactis* HN019, *Lactobacillus reuteri* ATCC55730, *Lactobacillus rhamnosus*, *Lactobacillus casei* DN-114 001, *Bifidobacterium lactis* Bb-12, or combinations thereof.

In another embodiment, the active pharmaceutical ingredient comprises active drug substances used in the treatment of addictive disorders, such as, for example: nicotine, nicotine polacrilex, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides, ganglioside derivatives, tirilazad, riluzole, xaliproden, hydroxybutyric acid, amifampridine, or combinations thereof. In one embodiment described herein, the active pharmaceutical ingredient comprises one or more of nicotine (~2 mg), acesulfame potassium, magnesium oxide, menthol, peppermint oil, xylitol, sodium bicarbonate, sodium carbonate, or combinations thereof.

In another embodiment, the active pharmaceutical ingredient can comprise those found in energy drinks, including caffeine, taurine, ginko biloba, glucuronolactone, inositol, niacin, niacinamide, D-pantothenol, panax ginseng root extract, pyridoxine HCl, vitamin B12, cyanocobalamin, riboflavin, guarana, L-carnitine, or combinations thereof.

In another embodiment, the pharmaceutical composition can comprise vitamins or minerals. "Vitamins" as used herein refers to nutraceuticals or pharmaceutical ingredients comprising organic substances that are typically considered essential for the normal growth and activity of a subject (e.g., a human or non-human animal patient to whom the composition is to be administered). Non-limiting examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, para-aminobenzoic acid or combinations thereof.

In some embodiments, the active pharmaceutical ingredient is a pharmaceutical a nutraceutical. Examples of nutraceuticals include, but are not limited to, amino acids, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfinates, phytosterols, anthraquinones, capsaicin, piperine, chlorophyll, betaine, oxalic acid, acetyl-L-carnitine, allantoin, androstenediol, androstendione, betaine (trimethylglycine), caffeine, calcium pyruvate (pyruvic acid), carnitine, carnosine, carotene, carotenoid, choline, chlorogenic acid, cholic acid, chondroitin sulfate, chondroitin sulfate, cholestan, chrysin, coenzyme Q10, conjugated linoleic acid, corosolic acid, creatine, dehydroepiandrosterone, dichlorophen, diindolymethane, dimethylglycine, dimercapto succinic acid, ebselen, ellagic acid, enzymes, fisetin, formononetin, glucaric acid (glucarate), glucosamine (HCl or sulfate), glucosamine (N-acetyl), glutathione, hesperidine, hydroxy-3-methylbutyric acid, 5-hydroxytryptophan, indole-3-carbinol, inositol, isothiocyanates, linolenic acid-gamma, lipoic acid (alpha), melatonin, methylsulfonylmethane, minerals, naringin, pancreatin, para-aminobenzoic acid, paraben (methyl or propyl), phenolics, phosphatidylcholine, phosphatidylserine, phospholipids, phytosterols, progesterone, pregnenolone, omega-3 fatty acids, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta, and gamma), zeaxanthin, gingko biloba, ginger, cat's claw, hypericum, aloe vera, evening primrose, garlic, ginseng, capsicum, dong quai, ginseng, feverfew, fenugreek, echinacea, green tea, marshmallow, saw palmetto, tea tree oil, fish oil, psyllium, kava-kava, licorice root, mahonia aquifolium, hawthorne, tumeric, witch hazel, yohimbe, aleurain, mistletoe, bilberry, bee pollen, peppermint oil, beta-carotene, genistein, lutein, lycopene, polyphenols, and the like. Further examples of suitable nutraceuticals include those listed in *Handbook of Nutraceuticals and Functional Foods*, Robert E. C. Wildman, Ed., CRC Press (2001), which is incorporated by reference herein for the teachings related to nutraceuticals.

In another embodiment, the active pharmaceutical ingredients described herein may comprise pharmaceutically acceptable salts of any of the above mentioned active drug substances. The term "pharmaceutically acceptable salts" of an active pharmaceutical ingredient includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, the active pharmaceutical ingredient may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the active pharmaceutical ingredient may be in any of its crystalline, polymorphous, semi-crystalline, amorphous or polyamorphous forms or mixtures thereof.

In another embodiment, an active pharmaceutical ingredient comprises about 0% to about 6% by weight of the matrix fill, including each integer within the specified range. In another embodiment, the active pharmaceutical ingredient comprises about 0.25% to about 5%, about 0.5% to about 4%, about 0.75% to about 3%, or about 1% to about 2% by weight of the matrix fill. In one aspect, the active pharmaceutical ingredient comprises about 0%, about 1%, about 2%, about 3%, about 4%, about 5%, or about 6% by weight of the matrix fill. In one aspect, the active pharmaceutical ingredient comprises about 1.6% by weight of the fill. In one aspect, the active pharmaceutical ingredient comprises about 1%, about 1.5%, about 2%, or about 2.5% by weight of the fill.

In another embodiment, the active pharmaceutical ingredient comprises dextromethorphan hydrobromide having a weight percentage of about 0% to about 5% by weight of the matrix fill, including each integer within the specified range. In one aspect, dextromethorphan hydrobromide comprises about 0.25% to about 5%, about 0.5% to about 4%, about 0.75% to about 3%, or about 0.75% to about 2% by weight of the matrix fill. In another aspect, dextromethorphan hydrobromide comprises about 0%, about 1%, about 2%, about 3%, about 4%, or about 5% by weight of the matrix fill. In one aspect, dextromethorphan hydrobromide comprises about 1% by weight of the fill. In one aspect, dextromethorphan hydrobromide comprises about 0.50%, about 0.74%, or about 1.25% by weight of the matrix fill.

In another embodiment, the active pharmaceutical ingredient comprises menthol at a weight percentage of about 0% to about 2% by weight of the matrix fill, including each integer within the specified range. In one embodiment, menthol comprises about 0.1% to about 1.75%, about 0.2% to about 1.5%, about 0.3% to about 1.25%, or about 0.4% to about 1% by weight of the matrix fill. In another aspect, menthol comprises about 0%, about 0.25%, about 0.5%, about 0.75%, about 1.25%, about 1.5%; about 1.75%; or about 2% by weight of the matrix fill. In one aspect, menthol comprises about 0.5% by weight of the fill. In one aspect, menthol comprises about 0.40%, about 0.45%, about 0.55% or about 0.6% by weight of the fill.

In another embodiment, the ratio of the active pharmaceutical ingredient to the remaining fill components in the matrix fill comprises about 1:10 to about 1:100, including each ratio within the specified range. In one embodiment, the ratio of active pharmaceutical ingredient to the remaining fill components in the fill is about 1:20 to about 1:80, about 1:30 to about 1:70, or about 1:40 to about 1:70. In one aspect, the ratio of active pharmaceutical ingredient to the remaining fill components in the matrix fill is about 1:10, about 1:20, about 1:30, about 1:40, about 1:50, about 1:60, about 1:70, about 1:80, about 1:90, or about 1:100. In another aspect, the ratio of active pharmaceutical ingredient to the remaining fill components in the fill is about 1:63. In another aspect, the ratio of active pharmaceutical ingredient to the remaining fill components in the matrix fill is about 1:60, about 1:62, about 1:64, or about 1:65.

In another embodiment, the ratio of the active pharmaceutical ingredient to the total hydrophilic vehicle in the matrix fill comprises about 1:10 to about 1:50, including each ratio within the specified range. In one embodiment, the ratio of active pharmaceutical ingredient to the total hydrophilic vehicle in the matrix fill comprises about 1:15 to about 1:45, or about 1:20 to about 1:40. In one aspect, the ratio of active pharmaceutical ingredient to the total hydrophilic vehicle is about 1:10, about 1:20, about 1:30, about 1:40, or about 1:50. In another aspect, the ratio of active pharmaceutical ingredient to the total hydrophilic vehicle in the matrix fill is about 1:24. In another aspect, the ratio of active pharmaceutical ingredient to the total hydrophilic vehicle in the matrix fill is about 1:20, about 1:21, about 1:22, about 1:23, about 1:25, or about 1:26.

In another embodiment, the ratio of the active pharmaceutical ingredient to the propylene glycol in the matrix fill comprises about 1:1 to about 1:10, including each ratio within the specified range. In one embodiment, the ratio active pharmaceutical ingredient to propylene glycol in the fill is about 1:1 to about 1:9, about 1:2 to about 1:8, about 1:4 to about 1:7, or about 1:5 to about 1:6. In one aspect, the ratio of active pharmaceutical ingredient to propylene glycol in the matrix fill is about 1:1, about 1:2, about 1:3, about 1:4, about 1:5, or about 1:6. In another aspect, the ratio of active pharmaceutical ingredient to propylene glycol in the fill is about 1:5. In another aspect, the ratio of active pharmaceutical ingredient to propylene glycol in the matrix is about 1:2, about 1:3, about 1:4, or about 1:6.

In another embodiment described herein, the total mass of the matrix fill of the pharmaceutical composition described herein that comprises an active pharmaceutical ingredient described herein is from about 400 mg to about 1600 mg, including all integers within the specified range. In one aspect, the total mass of the matrix fill mass is about 400 mg. In another aspect, the total mass of the matrix fill mass is about 500 mg. In one aspect, the total mass of the matrix fill mass is about 600 mg. In another aspect, the total mass of the matrix fill mass is about 700 mg. In another aspect, the total mass of the matrix fill mass is about 800 mg. In another aspect, the total mass of the matrix fill mass is about 900 mg. In another aspect, the total mass of the matrix fill mass is about 1000 mg. In another aspect, the total mass of the matrix fill mass is about 1100 mg. In another aspect, the total mass of the matrix fill mass is about 1200 mg. In another aspect, the total mass of the matrix fill mass is about 1300 mg. In another aspect, the total mass of the matrix fill mass is about 1400 mg. In another aspect, the total mass of the matrix fill mass is about 1500 mg. In another aspect, the total mass of the matrix fill mass is about 1600 mg.

TABLE 3

Exemplary Liquisoft Composition

| Component | Exemplary Component | Weight Percentage (%) |
|---|---|---|
| Capsule Shell Formulation | | |
| Polymers | Gelatin, 150 Bloom | 19.3 |
| | Gelatin, 100 Blom | 8.3 |
| | Hydrolyzed Collagen | 4.9 |
| Plasticizers | Maltitol | 16.8 |
| | Glycerol | 24 |
| | Xylitol | 2.6 |
| Sweetener(s) | Sucralose | 0.2 |
| Polymer Modifiers | Citric Acid | 0.5 |
| Coloring | FD&C Food colorings | 0.1 |
| Solvent | Water | 23 |
| TOTAL | | 100% |
| Matrix Fill Formulation | | |
| Hydrophilic Vehicles | Propylene Glycol | 8.0 |
| | Polyethylene Glycol 400 | 19.5 |
| | Polyvinylpyrrolidone K30 | 1.2 |
| Flavorings | Citric Acid | 1.0 |
| | Lactic Acid | 1.0 |
| | Sodium Citrate | — |
| | Orange Flavor PB72 | 1.6 |
| Sweeteners | Mannitol | — |
| | Acesulfame potassium | 0.6 |
| | Glycyrrhizic acid salts (MagnaSweet ®) | — |
| | Maltitol | 55.1 |
| | Sucralose | 0.6 |
| Excipients | e.g., γ-cyclodextrin | 2.2 |
| Solvent | Water | 7.5 |
| Active Pharmaceutical Ingredients (API) | Dextromethorphan Hydrobromide | 1.6 |
| | Menthol | 0.1 |
| TOTAL | | 100% |

One embodiment described herein is an oral pharmaceutical composition suitable for chewing, sucking, or buccal dissolution comprising the composition in Table 3.

In one embodiment, the pharmaceutical composition described herein, comprises an active pharmaceutical ingredient of about 0.5 mg to about 5000 mg, including each integer within the specified range.

In one embodiment, the pharmaceutical composition described herein, comprises an active pharmaceutical ingredient of about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, about 5 mg, about 5.25 mg, about 5.5 mg, about 5.75 mg, about 6 mg, about 6.25 mg, about 6.5 mg, about 6.75 mg, about 7 mg, about 7.25 mg, about 7.5 mg, about 7.75 mg, about 8 mg, about 8.25 mg, about 8.5 mg, about 8.75 mg, about 9 mg, about 9.25 mg, about 9.5 mg, about 9.75 mg, or about 10 mg, or even greater.

In another embodiment described herein, the pharmaceutical composition described herein, comprises an active pharmaceutical ingredient of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, or about 1000 mg, or even greater.

In another embodiment described herein, the pharmaceutical composition described herein, comprises an active pharmaceutical ingredient of about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, about 2000 mg, about 2050 mg, about 2100 mg, about 2150 mg, about 2200 mg, about 2250 mg, about 2300 mg, about 2350 mg, about 2400 mg, about 2450 mg, about 2500 mg, about 2550 mg, about 2600 mg, about 2650 mg, about 2700 mg, about 2750 mg, about 2800 mg, about 2850 mg, about 2900 mg, about 2950 mg, about 3000 mg, about 3050 mg, about 3100 mg, about 3150 mg, about 3200 mg, about 3250 mg, about 3300 mg, about 3350 mg, about 3400 mg, about 3450 mg, about 3500 mg, about 3550 mg, about 3600 mg, about 3650 mg, about 3700 mg, about 3750 mg, about 3800 mg, about 3850 mg, about 3900 mg, about 3950 mg, about 4000 mg, about 4050 mg, about 4100 mg, about 4150 mg, about 4200 mg, about 4250 mg, about 4300 mg, about 4350 mg, about 4400 mg, about 4450 mg, about 4500 mg, about 4550 mg, about 4600 mg, about 4650 mg, about 4700 mg, about 4750 mg, about 4800 mg, about 4850 mg, about 4900 mg, about 4950 mg, or about 5000 mg, or even greater.

In another embodiment described herein, the dosage form can be administered, for example, 1×, 2×, 3×, 4×, 5×, 6×, 7×, or 8×, per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, or even longer. One or more dosage forms can be administered until the patient, subject, mammal, mammal in need thereof, human, or human in need thereof, does not require treatment, prophylaxis, or amelioration of any disease or condition such as, for example, pain. In some aspects, the dosage form may be co-administered with other pharmaceutical compositions until the patient, subject, mammal, mammal in need thereof, human, or human in need thereof, does not require treatment, prophylaxis, or amelioration of any disease or condition including but not limited to pain or illness.

In one embodiment described herein, the active pharmaceutical ingredient comprises dextromethorphan hydrobromide having a dose of about 5 mg to about 200 mg, including all integers within the specified range. In one aspect, the dose of dextromethorphan hydrobromide is about 5 mg. In one aspect, the dose of dextromethorphan hydrobromide is about 10 mg. In another aspect, the dose of dextromethorphan hydrobromide is about 15 mg. In another aspect, the dose of dextromethorphan hydrobromide is about 20 mg. In another aspect, the dose of dextromethorphan hydrobromide is about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg.

In one embodiment described herein, the active pharmaceutical ingredient comprises dextromethorphan hydrobromide and menthol, wherein the dose of dextromethorphan hydrobromide is as described of, and the dose of menthol is about 1 mg to about 10 mg, including all integers within the specified range. In one aspect, the dose of menthol is about 0.09 mg. In one aspect, the dose of menthol is about 1 mg. In another aspect, the dose of menthol is about 2 mg. In another aspect, the dose of menthol is about 3 mg. In another aspect, the dose of menthol is about 3 mg. In another aspect, the dose of menthol is about 4 mg. In another aspect, the dose of menthol is about 5 mg. In another aspect, the dose of menthol is about 5 mg. In another aspect, the dose of menthol is about 6 mg. In another aspect, the dose of menthol is about 7 mg. In another aspect, the dose of menthol is about 8 mg. In another aspect, the dose of menthol is about 9 mg. In another aspect, the dose of menthol is about 10 mg.

In one embodiment, the total dosage of dextromethorphan hydrobromide and menthol administered in a 24-hour period is about 20 mg to about 200 mg. In one aspect, the total dosage of dextromethorphan hydrobromide and menthol administered in a 24-hour period is about 30 mg, about 40 mg, about 50 mg, about 60 mg, about 70 mg, about 80 mg, about 90 mg, about 100 mg, about 110 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg.

In one embodiment, the total dosage of dextromethorphan hydrobromide and menthol administered in a 24-hour period is about 20 mg to about 160 mg per 24-hour period including all iterations of integers within the specified range. In another embodiment, the total dosage of dextromethorphan hydrobromide and menthol administered in a 24-hour period is about 20 mg to about 40 mg per 24-hour period including all iterations of integers within the specified range. In another embodiment, the total dosage of dextromethorphan hydrobromide and menthol administered in a 24-hour period is about 30 mg to about 50 mg per 24-hour period including all iterations of integers within the specified range. In another embodiment, the total dosage of dextromethorphan hydrobromide and menthol administered in a 24-hour period is about 40 mg to about 60 mg per 24-hour period including all iterations of integers within the specified range. In another embodiment, the total dosage of dextromethorphan hydrobromide and menthol administered in a 24-hour period is about 50 mg to about 80 mg per 24-hour period including all iterations of integers within the specified range. In another embodiment, the total dosage of dextromethorphan hydrobromide and menthol administered in a 24-hour period is about 60 mg to about 90 mg per 24-hour period including all iterations of integers within the specified range. In another embodiment, the total dosage of dextromethorphan hydrobromide and menthol administered in a 24-hour period is about 70 mg to about 100 mg per 24-hour period including all iterations of integers within the specified range. In another embodiment, the total dosage of dextromethorphan hydrobromide and menthol administered in a 24-hour period is about 80 mg to about 110 mg per 24-hour period including all iterations of integers within the specified range. In another embodiment, the total dosage of dextromethorphan hydrobromide and menthol administered in a 24-hour period is about 90 mg to about 120 mg per 24-hour period including all iterations of integers within the specified range. In another embodiment, the total dosage of dextromethorphan hydrobromide and menthol administered in a 24-hour period is about 100 mg to about 130 mg per 24-hour period including all iterations of integers within the specified range. In another embodiment, the total dosage of dextromethorphan hydrobromide and menthol administered in a 24-hour period is about 110 mg to about 140 mg per 24-hour period including all iterations of integers within the specified range. In another embodiment, the total dosage of dextromethorphan hydrobromide and menthol administered in a 24-hour period is about 120 mg to about 150 mg per 24-hour period including all iterations of integers within the specified range. In another embodiment, the total dosage of dextromethorphan hydrobromide and menthol administered in a 24-hour period is about 130 mg to about 160 mg per 24-hour period including all iterations of integers within the specified range.

In another embodiment, the total dosage of dextromethorphan hydrobromide and menthol administered in a 24-hour period is about 20 mg to about 160 mg and is effective for the treatment of cough or illness is administered in equal daily doses. In one aspect, 20 mg of dextromethorphan hydrobromide and menthol is administered 2 times daily for a total of 40 mg to reach a desired therapeutic efficacy. In another aspect, 20 mg of dextromethorphan and menthol is administered 4 times daily for a total of 80 mg to reach a desired therapeutic efficacy. In another aspect, 20 mg of dextromethorphan and menthol is administered 6 times daily for a total of 120 mg to reach a desired therapeutic efficacy. In another aspect, 20 mg of dextromethorphan and menthol is administered 8 times daily for a total of 160 mg to reach a desired therapeutic efficacy.

In one embodiment, the dosage can contain an amount of dextromethorphan hydrobromide effective for treatment, amelioration, prophylaxis, or reducing the onset of or symptoms of mild, moderate, or severe cold and cough.

In another embodiment, the dosage can contain an amount of dextromethorphan hydrobromide and an amount of one or more nasal decongestants, antitussives, expectorants, or antihistamines, or a mixture or combination thereof for the treatment, amelioration, prophylaxis, or reducing the onset of or symptoms of a cough or cold.

In one embodiment described herein, the active pharmaceutical ingredient comprises thymol having a dose of about 0.0005 mg to about 0.002 mg, including all integers within the specified range. In one aspect, the dose of thymol is about 0.0005 mg. In one aspect, the dose of thymol is about 0.00075 mg. In another aspect, the dose of thymol is about 0.001 mg. In another aspect, the dose of thymol is about 0.0015 mg. In another aspect, the dose of thymol is about 0.002 mg. In another aspect, the dose of thymol is about 0.0005 mg, about 0.0006 mg, about 0.0007 mg, about 0.0008 mg, about 0.0009 mg, about 0.001 mg, or about 0.002 mg.

In one embodiment described herein, the active pharmaceutical ingredient comprises thymol and menthol, wherein the dose of thymol is as described of, and the dose of menthol is about 1 mg to about 10 mg, including all integers within the specified range. In one aspect, the dose of menthol is about 0.09 mg. In one aspect, the dose of menthol is about 1 mg. In another aspect, the dose of menthol is about 2 mg. In another aspect, the dose of menthol is about 3 mg. In another aspect, the dose of menthol is about 3 mg. In another aspect, the dose of menthol is about 4 mg. In another aspect, the dose of menthol is about 5 mg. In another aspect, the dose of menthol is about 5 mg. In another aspect, the dose of menthol is about 6 mg. In another aspect, the dose of menthol is about 7 mg. In another aspect, the dose of menthol is about 8 mg. In another aspect, the dose of menthol is about 9 mg. In another aspect, the dose of menthol is about 10 mg.

In one embodiment, the dosage can contain an amount of thymol effective for treatment, amelioration, prophylaxis, or reducing the onset of or symptoms of dry mouth, halitosis, stained teeth, oral pain, or loss of enamel.

In another embodiment, the dosage can contain an amount of thymol and an amount of one or more chlorohexidine, ethanol or a mixture or combination thereof for the treatment, amelioration, prophylaxis, or reducing the onset of or symptoms of dry mouth, halitosis, stained teeth, oral pain, or loss of enamel.

In one embodiment described herein, the active pharmaceutical ingredient comprises nicotine polacrilex having a dose of about 2 mg to about 80 mg, including all integers within the specified range. In one aspect, the dose of nicotine polacrilex is about 10 mg to about 70 mg, about 20 mg to about 60 mg, or about 30 mg to about 50 mg. In another aspect, the dose of nicotine polacrilex is about 2 mg, about 4 mg, about 6 mg, about 8 mg, about 10 mg, about 20 mg, about 40 mg, about 60 mg, or about 80 mg.

In one embodiment, the dosage can contain an amount of nicotine polacrilex effective for treatment, amelioration, prophylaxis, or reducing the onset of or symptoms of urge to smoke.

In another embodiment, the dosage can contain an amount of nicotine polacrilex and an amount of one or more bupropion, varenicline or a mixture or combination thereof for the treatment, amelioration, prophylaxis, or reducing the onset of symptoms of urge to smoke.

In one embodiment described herein, the active pharmaceutical ingredient comprises bismuth subsalicylate having a dose of about 44 mg to about 4,192 mg, including all integers within the specified range. In one aspect, the dose of bismuth subsalicylate is about 50 mg to about 4000 mg, about 75 mg to about 3,500 mg, or about 100 mg to about 3,000 mg. In another aspect, the dose of bismuth subsalicylate is about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,500 mg, about 2,000 mg, about 2,500 mg, about 3,000 mg about 3,500 mg, or about 4,000 mg.

In one embodiment, the dosage can contain an amount of bismuth subsalicylate effective for treatment, amelioration, prophylaxis, or reducing the onset of inflammation of the gastrointestinal tract, neoplasia, hyperthyroidism, hypercalcemia, hyperparathyroidism, parathyroid carcinoma, indigestion, heartburn, irritable bowels, constipation, or diarrhea.

In another embodiment, the dosage can contain an amount of bismuth subsalicylate and an amount of one or more of cimetidine, ranitidine, famotidine, ondansetron, omeprazole, lansoprazole, rabeprazole, esomeprazole, pantoprazole, calcium supplements, calcium hydroxide, alluminum hydroxide, magnesium hydroxide, or a mixture or combination thereof for the treatment, amelioration, prophylaxis, or reducing the onset of inflammation of the gastrointestinal tract, neoplasia, hyperthyroidism, hypercalcemia, hyperparathyroidism, parathyroid carcinoma, indigestion, heartburn, irritable bowels, constipation, diarrhea.

The concentration of the active pharmaceutical ingredient in the pharmaceutical composition depends on the specific active pharmaceutical ingredient, the disease to be treated, the condition of the patient, the age, and gender of the patient, etc. The active pharmaceutical ingredient may be a well-known active pharmaceutical ingredient and a person having ordinary skill in the art will be able to find information as to the dosage of each active drug substance and, accordingly, will know how to determine the amount of each active drug substance in the pharmaceutical composition.

Another embodiment described herein is a method for treating, retarding the progression of, prophylaxis of, delaying the onset of, ameliorating, reducing the symptoms of, or promoting health, including but not limited to of one or more of pain, inflammation, cough, cold, fever, flu, inflammation of the gastrointestinal tract, neoplasia, hyperthyroidism, hypercalcemia, hyperparathyroidism, parathyroid carcinoma, indigestion, heartburn, irritable bowels, constipation, diarrhea, insomnia, dry mouth, halitosis, stained teeth, oral pain, loss of enamel, urge to smoke, fatigue, or malaise comprising administering to a subject in need thereof an oral pharmaceutical composition suitable for chewing, sucking, or buccal dissolution as described herein.

Another embodiment described herein is a composition for treating, retarding the progression of, prophylaxis of, delaying the onset of, ameliorating, reducing the symptoms of, or promoting health, including but not limited to of one or more of pain, inflammation, cough, cold, fever, flu, inflammation of the gastrointestinal tract, neoplasia, hyperthyroidism, hypercalcemia, hyperparathyroidism, parathyroid carcinoma, indigestion, heartburn, irritable bowels, constipation, diarrhea, insomnia, dry mouth, halitosis, stained teeth, oral pain, loss of enamel, urge to smoke, fatigue, or malaise comprising administering to a subject in need thereof an oral pharmaceutical composition suitable for chewing, sucking, or buccal dissolution as described herein.

Another embodiment described herein is a method for treating, retarding the progression of, prophylaxis of, delaying the onset of, ameliorating, or reducing the symptoms of cough, cold, or congestion comprising the administration of a therapeutically effective amount of dextromethorphan hydrobromide comprising any one of the pharmaceutical compositions described herein to a subject with cough, wherein the administration is sufficient to achieve a reduction of cough, congestion or cold related symptoms.

In one aspect, after administration of any one the pharmaceutical compositions described herein, the subject experiences the side effects described herein at a rate of less than about 10%. In another aspect, the subject experiences the side effects described herein at a rate of less than about 2%, about 5%, about 10%, about 15%, about 20%, about 25%, about 30%, about 35%, about 45%, about 50%, about 60%, about 70%, about 80%, or about 90%.

Another embodiment described herein is a method for manufacturing the oral pharmaceutical composition comprising the steps of: (a) preparing a gel fill composition comprising a first solution and a second solution wherein: (i) the first solution comprises polyvinylpyrrolidone K30, orange flavor, citric acid, sucralose, acesulfame potassium, lycasin and water, one or more excipients in one or more solvents and mixed at a temperature no greater than 55° C. until dissolved and clear; (ii) the second solution comprises polyethylene glycol 400, propylene glycol and lactic acid and mixed until dissolved and clear; where the composition comprises one or more film forming polymers, one or more plasticizers, one or more sweeteners, one or more excipients in one or more solvents; (iii) adding dextromethorphan hydrobromide and menthol to the second solution and mixing the first solution and heating to no greater than 55° C. until dissolved; and (iv) combining the first solution with the second solution and purging with nitrogen; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a method for manufacturing the oral pharmaceutical composition of claims comprising the steps of: (a) preparing a gel fill composition comprising a first gel fill solution and a second gel fill solution, wherein (i) the first gel fill solution comprises one or more hydrophilic vehicle, sweetener, flavor, thymol, in one or more solvents and is mixed at a temperature between 30-50° C. until dissolved; (ii) the second gel fill solution comprises one or more hydrophilic vehicles and menthol and is mixed at a temperature between 30-50° C. until dissolved; and (iv) combining the first gel fill solution and the second gel fill solution, adding flavor and mixing for at least 25 minutes; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a method for manufacturing the oral pharmaceutical composition of claims comprising the steps of: (a) preparing a gel fill composition comprising a first solution, a flavor solution, and a sweetener solution wherein: (i) the first solution comprises one or more hydrophilic vehicles, thickening agents, flavors, and excipients and is mixed at a temperature between 30-70° C. until dissolved; (ii) the flavor solution comprises one or more hydrophilic vehicle and flavor and is mixed at a temperature between 30-70° C. until dissolved; (iii) the sweetener solution comprises one or more sweetener in one or more solvents and nicotine and mixing until dissolved; and (iv) combining the first solution, flavor solution and sweetener solution and mixing to homogenize; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

Another embodiment described herein is a method for manufacturing an oral pharmaceutical composition comprising the steps of: (a) preparing a gel fill composition comprising a color solution, a flavor solution and a gel solution wherein: (i) the color solution comprises one or more colors and excipient in one or more solvents and mixed at a temperature between 30-50° C. until dissolved; (ii) the flavor solution comprises one or more of plasticizer, menthol and flavor and mixed at a temperature between 30-50° C. until dissolved; (iii) the gel solution comprises soaking one or more film forming polymer, plasticizer, sweeteners in one or more solvents, then heated at a temperature between 30-70° C. until dissolved; (iv) combining the color solution, flavor solution, and gel solution and adding bismuth subsalicylate and mixing at a temperature of 20-60° C. until dissolved; (b) preparing a gel mass composition comprising one or more film forming polymers, one or more plasticizers, one or more sweeteners, one or more excipients and one or more solvents; (c) casting the gel composition into films or ribbons using heat-controlled drums or surfaces; and (d) forming a soft dosage form comprising a liquid matrix fill using rotary die encapsulation technology.

In another embodiment described herein, one or more of the oral pharmaceutical compositions described herein are contained and dispensed in a kit comprising a tamper evident packaging. The term "tamper evident" or "tamper resistant" refers to a packaging of any kind that readily displays or permits an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also comprise a dessicant and packing filler material to prevent the contents from shifting or rattling. The packaging may also contain appropriate instructions for prescribing, instructions for use, warnings, or other appropriate information. In another aspect, the packaging may contain at least one daily regimen for the oral pharmaceutical composition.

Another embodiment described herein is a kit for dispensing any of the oral pharmaceutical compositions described herein comprising: (a) at least one oral pharmaceutical composition; (b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally (c) at least one daily regimen for the oral pharmaceutical composition; and (d) an insert comprising instructions or prescribing information for the oral pharmaceutical composition. In one aspect described herein, the kit is useful for treating pain, inflammation, cough, cold, sinusitis, throat or bronchial irritation, fever, flu, inflammation of the gastrointestinal tract, neoplasia, hyperthyroidism, hypercalcemia, hyperparathyroidism, parathyroid carcinoma, indigestion, heartburn, irritable bowels, constipation, diarrhea, insomnia, dry mouth, halitosis, stained teeth, oral pain, loss of enamel, cessation of urge to smoke, fatigue, or malaise according to any of the methods described herein.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Exemplary capsule shell and matrix compositions useful for producing Liquisoft capsules as described herein are shown in Table 4. Composition components are set forth by weight percentage of the total weight of the composition. Such compositions may be encapsulated using rotary die encapsulation as described herein.

Formulas 1 and 2 were the first shell formulations developed to achieve faster disintegration time and prevent cross-linking of the gelatin shell with matrix fill components.

TABLE 4

Exemplary Liquisoft Composition
Capsule Shell Formulation

| Component | Formula 1 | Formula 2 |
|---|---|---|
| Gelatin, 250 Bloom | 24.3 | — |
| Gelatin, 150 Bloom | — | 29.2 |
| Gelatin, 100 Bloom | 4.9 | — |
| Gelatin Hydrolysate | — | — |
| Hydrolyzed Collagen | — | — |
| Powdered Cellulose | 1.9 | — |
| Maltitol | — | 25.7 |
| Glycerol | 32.0 | 19.1 |
| Xylitol | 4.8 | — |
| Sucralose | — | — |

TABLE 4-continued

| Exemplary Liquisoft Composition Capsule Shell Formulation | | |
|---|---|---|
| Component | Formula 1 | Formula 2 |
| Citric Acid | — | 0.5 |
| Flavors | — | 0.5 |
| Water | 32.3 | 25.0 |
| TOTAL | 100% | 100% |
| VISCOSITY | — | 3497 cP |

Example 2

Exemplary capsule shell and matrix compositions useful for producing Liquisoft capsules as described herein are shown in Table 5. Composition components are set forth by weight percentage of the total weight of the composition. Such compositions may be encapsulated using rotary die encapsulation as described herein.

Formulas 3, 4 and 5 were developed to include citric acid, glycine and gelatin hydrolysate to inhibit crosslinking, 250 Bloom gelatin was substituted for 150 Bloom gelatin, and maltitol was used as the bulk sweetener.

TABLE 5

| Exemplary Liquisoft Composition Capsule Shell Formulation | | | |
|---|---|---|---|
| Component | Formula 3 | Formula 4 | Formula 5 |
| Gelatin, 250 Bloom | — | — | — |
| Gelatin, 150 Bloom | 29.0 | 29.0 | 24.5 |
| Gelatin, 100 Bloom | — | — | 4.9 |
| Gelatin Hydrolysate | 4.8 | — | — |
| Hydrolyzed Collagen | — | — | — |
| Powdered Cellulose | — | — | — |
| Maltitol | 18.1 | 18.1 | — |
| Glycerol | 18.9 | 18.9 | 32.3 |
| Xylitol | — | — | 4.8 |
| Mannitol | 2.4 | 2.4 | — |
| Sucralose | 0.2 | 0.2 | 0.2 |
| Citric Acid | 0.5 | 0.5 | 0.5 |
| Glycine | — | 4.8 | — |
| Flavors | — | — | — |
| Water | 25.8 | 25.8 | 32.5 |
| TOTAL | 100% | 100% | 100% |
| VISCOSITY | 4544 cP | 2747 cP | 1627 cP |

Example 3

A dissolution study was performed using soft gel capsules comprising the pharmaceutical compositions shown in Tables 4 and 5. The compositions of Formula 1 and Formula 2 served as controls. The time for complete dissolution and average viscosity of each formula was recorded. Further compositions were formulated to achieve a higher viscosity.

TABLE 7

| Exemplary Liquisoft Composition | | |
|---|---|---|
| Formula | Complete Dissolution (min) | Average Viscosity (cP) |
| Formula 1 | A mass of gel remains after 20 minutes | NT |
| Formula 2 | 20 | 3497 |
| Formula 3 | 19.5 | 4544 |
| Formula 4 | 18 | 2747 |
| Formula 5 | 17.5 | 1627 |

Example 4

Exemplary capsule shell and matrix compositions useful for producing Liquisoft capsules as described herein are shown in Table 6. Composition components are set forth by weight percentage of the total weight of the composition. Such compositions may be encapsulated using rotary die encapsulation as described herein.

Formula 6 had a higher viscosity due to a total of 39% gelatin. Application batches were made using Formula 6 and Formula 7 shell formulas as placebo and active fill formulations. Capsules were evaluated but required further optimization to improve chewability.

TABLE 6

| Exemplary Liquisoft Composition Capsule Shell Formulation | | |
|---|---|---|
| Component | Formula 6 | Formula 7 |
| Gelatin, 250 Bloom | — | — |
| Gelatin, 150 Bloom | 27.3 | 31.5 |
| Gelatin, 100 Bloom | 7.9 | — |
| Gelatin Hydrolysate | 5.0 | — |
| Hydrolyzed Collagen | — | — |
| Powdered Cellulose | — | — |
| Maltitol | — | 16.1 |
| Glycerol | 32.0 | 19.2 |
| Xylitol | 4.8 | — |
| Mannitol | — | — |
| Sucralose | 0.2 | 0.2 |
| Citric Acid | 0.5 | 0.5 |
| Glycine | — | 5.0 |
| Flavors | — | — |
| Water | 22.0 | 27.5 |
| TOTAL | 100% | 100% |
| VISCOSITY | 13,418 cP | 5,748 cP |

Example 5

Exemplary capsule shell and matrix compositions useful for producing Liquisoft capsules as described herein are shown in Table 7. Composition components are set forth by weight percentage of the total weight of the composition. Such compositions may be encapsulated using rotary die encapsulation as described herein.

The composition of Formulas 8, 9, and 10 included increased amounts of 100 Bloom gelatin to minimize shell toughness. As seen in Table 7, increased amounts of 100 Bloom gelatin resulted in decreased viscosity but encapsulation was unsuccessful. Formula 10 was revised further.

TABLE 7

Exemplary Liquisoft Composition
Capsule Shell Formulation

| Component | Formula 8 | Formula 9 | Formula 10 |
|---|---|---|---|
| Gelatin, 250 Bloom | — | — | — |
| Gelatin, 150 Bloom | 14.2 | 18.7 | 19.8 |
| Gelatin, 100 Bloom | 14.2 | 12.5 | 13.1 |
| Gelatin Hydrolysate | 4.9 | 4.9 | 5.2 |
| Hydrolyzed Collagen | — | — | — |
| Powdered Cellulose | — | — | — |
| Maltitol | 15.7 | 16.7 | 18.8 |
| Glycerol | 18.9 | 20.2 | 20.6 |
| Xylitol | 0.5 | 0.5 | 5.2 |
| Mannitol | — | — | — |
| Sucralose | 0.5 | 0.5 | 0.2 |
| Citric Acid | 0.5 | 0.2 | 0.5 |
| Glycine | — | — | — |
| Flavors | — | — | — |
| Water | 30.6 | 25.8 | 16.6 |
| TOTAL | 100% | 100% | 100% |
| VISCOSITY | 2,628 cP | 1,899 cP | 8,376 cP |

Example 6

Exemplary capsule shell and matrix compositions useful for producing Liquisoft capsules as described herein are shown in Table 8. Composition components are set forth by weight percentage of the total weight of the composition. Such compositions may be encapsulated using rotary die encapsulation as described herein.

Formula 10 was revised to increase the amount of water to 20%, resulting in Formula 11. Formula 11 was encapsulated, but was further revised to reduce the viscosity. Hence, Formula 12 was developed whereby the amount of water was increased to 22% and the total amount of gelatin was limited to 31% resulting in a viscosity of approximately 4300 cP. Formula 12 was used for GMP batch manufacturing to evaluate the combination product.

TABLE 8

Exemplary Liquisoft Composition
Capsule Shell Formulation

| Component | Formula 11 | Formula 12 |
|---|---|---|
| Gelatin, 250 Bloom | — | — |
| Gelatin, 150 Bloom | 22.7 | 18.9 |
| Gelatin, 100 Bloom | 9.7 | 8.1 |
| Gelatin Hydrolysate | 5.0 | 5.1 |
| Hydrolyzed Collagen | — | — |
| Powdered Cellulose | — | — |
| Maltitol | 16.3 | 16.3 |
| Glycerol | 19.7 | 23.3 |
| Xylitol | 5.0 | 2.5 |
| Mannitol | — | — |
| Sucralose | 0.2 | 0.2 |
| Citric Acid | 0.5 | 0.5 |
| Glycine | — | — |
| Flavors | 0.5 | 0.5 |
| Water | 20.2 | 24.8 |
| TOTAL | 100% | 100% |
| VISCOSITY | 13,226 cP | 4,341 cP |

Example 7

Exemplary capsule shell and matrix compositions useful for producing Liquisoft capsules as described herein are shown in Table 9. Composition components are set forth by weight percentage of the total weight of the composition. Such compositions may be encapsulated using rotary die encapsulation as described herein.

Formula 13 was used for GMP batch manufacture.

TABLE 9

Exemplary Liquisoft Composition
Capsule Shell Formulation

| Component | Formula 13 |
|---|---|
| Gelatin, 250 Bloom | — |
| Gelatin, 150 Bloom | 19.3 |
| Gelatin, 100 Bloom | 8.3 |
| Gelatin Hydrolysate | — |
| Hydrolyzed Collagen | 4.9 |
| Powdered Cellulose | — |
| Maltitol | 16.8 |
| Glycerol | 24.0 |
| Xylitol | 2.6 |
| Mannitol | — |
| Sucralose | 0.2 |
| Citric Acid | 0.5 |
| Glycine | — |
| Flavors | 0.5 |
| Water | 22.7 |
| TOTAL | 100% |
| VISCOSITY | — |

Example 8

Exemplary capsule shell and matrix compositions useful for producing Liquisoft capsules as described herein are shown in Table 10. Composition components are set forth by weight percentage of the total weight of the composition. Such compositions may be encapsulated using rotary die encapsulation as described herein.

Formulas 14, 15, and 16 were the initial matrix prototypes for dextromethorphan hydrobromide (30 mg) and menthol (5 mg). Three different taste-masking agents were tested: mannitol, thaumatin (Talin®) and glycyrrhizic acid salts (MagnaSweet®). Thaumatin resulted in the most effective taste masking of the dextromethorphan hydrobromide, but resulted in a hazy appearance.

TABLE 10

Exemplary Liquisoft Composition
Matrix Formulation

| Component | Formula 14 | Formula 15 | Formula 16 |
|---|---|---|---|
| Propylene Glycol | 8.1 | 8.1 | 8.1 |
| Polyethylene Glycol 400 | 25.4 | 25.4 | 25.4 |
| Polyvinylpyrrolidone K30 | 1.5 | 1.5 | 1.5 |
| Maltitol | 50.0 | 50.0 | 50.0 |
| Sucralose | 0.6 | 0.6 | 0.6 |
| Citric Acid | 1.0 | 1.0 | 1.0 |
| Lactic Acid | 1.0 | 1.0 | 1.0 |
| Sodium Citrate | 1.0 | 1.0 | 1.0 |
| Mannitol | 3.0 | — | — |
| Thaumatin (Talin ®) | — | 3.0 | — |
| Glycyrrhizic acid salts (MagnaSweet ®) | — | — | 3.0 |
| Water | 5.0 | 5.0 | 5.0 |
| Dextromethorphan Hydrobromide | 3.0 | 3.0 | 3.0 |
| Menthol | 0.5 | 0.5 | 0.5 |
| TOTAL | 100% | 100% | 100% |

Example 9

Exemplary capsule shell and matrix compositions useful for producing Liquisoft capsules as described herein are shown in Table 11. Composition components are set forth by weight percentage of the total weight of the composition. Such compositions may be encapsulated using rotary die encapsulation as described herein.

Formulas 17, 18 and 19 were formulated with a reduced amount of dextromethorphan hydrobromide (10 mg) and menthol (5 mg). Thaumatin and glycyrrhizic acid salts were employed with the lower active pharmaceutical ingredient dose, individually and as a combination. Thaumatin was found to be the most effective at taste masking at the 10 mg dose and showed no precipitation (Formula 17). Thus, the glycyrrhizic acid salts were not further assessed for chemical stability. Thus, Formula 19 was formulated using thaumatin and used for excipient compatibility studies.

TABLE 11

Exemplary Liquisoft Composition Matrix Formulation

| Component | Formula 17 | Formula 18 | Formula 19 |
|---|---|---|---|
| Propylene Glycol | 8.4 | 8.4 | 8.4 |
| Polyethylene Glycol 400 | 26.6 | 26.6 | 26.6 |
| Polyvinylpyrrolidone K30 | 1.6 | 1.6 | 1.6 |
| Maltitol | 52.5 | 52.5 | 52.5 |
| Sucralose | 0.6 | 0.6 | 0.6 |
| Citric Acid | 1.6 | 1.6 | 1.0 |
| Lactic Acid | 1.6 | 1.6 | 1.0 |
| Sodium Citrate | 1.6 | 1.6 | 1.0 |
| Mannitol | — | — | — |
| Thaumatin (Talin ®) | 0.5 | — | 0.3 |
| Glycyrrhizic acid salts (MagnaSweet ®) | — | 0.6 | 0.2 |
| Water | 3.5 | 3.4 | 5.2 |
| Dextromethorphan Hydrobromide | 1.0 | 1.0 | 1.0 |
| Menthol | 0.5 | 0.5 | 0.5 |
| TOTAL | 100% | 100% | 100% |

Example 10

Formula 19 was used for excipient compatibility studies at stressed conditions (60° C. for 2 weeks) and the results are recorded in Table 12. A 3% loss occurred in the sample taken on the day of fill compounding and a 3% menthol loss occurred by the time the fill was encapsulated.

TABLE 12

Exemplary Liquisoft Composition

| Formula 19 (Talin-based fill) | Assay Dextromethorphan HBr | Menthol Degradation Products |
|---|---|---|
| $T_0$ | 99.9% | 97.4% Dextromethorphan: 0.01% |
| 1 week at 60° C. | 100.0% | 95.0% Dextromethorphan: 0.01% RRT 0.95: 0.03% |
| 2 weeks at 60° C. | 99.7% | 93.5% Dextromethorphan: 0.01% RRT 0.95: 0.03% |

Example 11

Exemplary capsule shell and matrix compositions useful for producing Liquisoft capsules as described herein are shown in Table 11. Composition components are set forth by weight percentage of the total weight of the composition. Such compositions were encapsulated using rotary die encapsulation as described herein.

Formulas 20 and 21 were used as batch formulations for active lots. Formula 20 is the formulation for the amount per capsule. Formula 21 is the formulation for the amount per batch.

TABLE 13

Exemplary Liquisoft Composition Matrix Formulation

| Component | Formula 20 | Formula 21 |
|---|---|---|
| Propylene Glycol | 8.4 | 8.4 |
| Polyethylene Glycol 400 | 25.6 | 26.6 |
| Polyvinylpyrrolidone K30 | 1.6 | 1.6 |
| Maltitol | 52.7 | 52.7 |
| Sucralose | 0.6 | 0.6 |
| Citric Acid | 1.0 | 1.0 |
| Lactic Acid | 1.0 | 1.0 |
| Sodium Citrate | — | — |
| Mannitol | — | — |
| Thaumatin (Talin ®) | 0.5 | 0.5 |
| Glycyrrhizic acid salts (MagnaSweet ®) | — | — |
| Water | 7.1 | 7.1 |
| Dextromethorphan Hydrobromide | 1.0 | 1.0 |
| Menthol | 0.5 | 0.5 |
| TOTAL | 100% | 100% |

Example 12

Formula 21 was encapsulated and gel parameters were determined. Encapsulation was performed using a 6.2 inch die with cavity of a 1 g square chewel capsule with target fill weight of 960 mg. The medicine was fed into the encapsulation machine using gravity feed from the 60 L tank. Medium chain triglycerides (MCT) were utilized as lubricant during encapsulation. The product was encapsulated at ambient temperatures and dried using a tumble drier. Gel parameters were recorded in Table 14.

TABLE 14

Exemplary Liquisoft Composition

| Encapsulation Parameters | Formula 21 |
|---|---|
| | Matrix Formulation |
| Gel Age (hrs) | 4-72 |
| Machine Die Speed (rpm) | 3.0 |
| Die pressure (psi) | 75 |
| Target Ribbon Thickness | 0.028 inches (Range 0.025-0.031 inches) |
| Fill weight (mg) | Target: 960 mg |
| | Alert Limits: 941-979 mg |
| | Control Limits: 912-1008 mg |

Example 13

Batch analytical data for Formula 21 was determined and recorded in Table 15. Results were recorded at time, T=0 and again at time, T=1 month at a temperature of 40° C. and 75% relative humidity (RH).

TABLE 15

Exemplary Liquisoft Composition Matrix Formulation

| Results at Initial T = 0 | Results at T = 1 months 40° C./75% RH |
|---|---|
| Assay Results | |
| Dextromethorphan Hbr 98.0% label claim | 100.4% label claim |
| Menthol 97.0% label claim | 100.4% label claim |
| Degradation Products Results | |
| Dextromethorphan Hbr RRT 1.09: 0.05% Total: 0.05% | RRT 1.09: 0.05% Total 0.05% |
| Menthol None Detected | RRT 1.15: 0.1%; RRT 1.73: 0.2%, Total 0.03% |
| Dissolution Study Results | |
| Dextromethorphan HBr | Dextromethorphan HBr |
| 15 minutes: 99% | 15 minutes: 99% |
| 30 minutes: 98% | 30 minutes: 98% |
| 45 minutes: 98% | 45 minutes: 98% |
| 60 minutes: 98% | 60 minutes: 98% |

Example 14

Exemplary capsule shell and matrix compositions useful for producing Liquisoft capsules as described herein are shown in Table 16. Composition components are set forth by weight percentage of the total weight of the composition. Such compositions were encapsulated using rotary die encapsulation as described herein.

TABLE 16

Exemplary Liquisoft Composition

| Component | Weight Percentage (%) |
|---|---|
| Capsule Shell Formulation | |
| Gelatin, 150 Bloom | 19.3 |
| Gelatin, 100 Bloom | 8.3 |
| Hydrolyzed Collagen | 4.9 |
| Glycerol | 24.0 |
| Maltitol | 16.8 |
| Xylitol | 2.6 |
| Sucralose | 0.2 |
| Citric Acid | 0.5 |
| Water | 23.0 |
| TOTAL | 100% |
| Matrix Fill Formulation | |
| Propylene Glycol | 8.4 |
| Polyethylene Glycol 400 | 26.6 |
| Polyvinylpyrrolidone K30 | 1.6 |
| Citric Acid | 1.0 |
| Lactic Acid | 1.0 |
| Sodium Citrate | — |
| Maltitol | 52.7 |
| Sucralose | 0.6 |
| Mannitol | — |
| Thaumatin (Talin ®) | 0.5 |
| Glycyrrhizic acid salts (MagnaSweet ®) | — |
| Water | 5.5 |
| Dextromethorphan Hydrobromide | 1.0 |
| Menthol | 0.5 |
| TOTAL | 100% |

Example 15

Exemplary capsule shell and matrix compositions useful for producing Liquisoft capsules as described herein are shown in Table 17. Composition components are set forth by weight percentage of the total weight of the composition. Such compositions may be encapsulated using rotary die encapsulation as described herein.

TABLE 17

Exemplary Liquisoft Compositions

| | Weight Percentage (%) | | | | | |
|---|---|---|---|---|---|---|
| Component | EX 1 | EX 2 | EX 3 | EX 4 | EX 5 | EX 6 |
| Capsule Shell Formulation | | | | | | |
| Polymers | 27 | 32 | 35 | 39 | 40 | 55 |
| Plasticizers | 61.5 | 49.5 | 43.8 | 34.5 | 29.5 | 29.9 |
| Polymer Modifiers | 1 | 0.1 | 0.7 | 0.7 | 1 | 1.3 |
| Solvent | 9.4 | 17.4 | 20.4 | 25.4 | 28.4 | 13.4 |
| Sweetener | 0.5 | 0.5 | 0.2 | 0.5 | 0.5 | 0.1 |
| Flavor | 0.5 | 0.5 | 0.5 | 0.5 | 0.5 | 0.5 |
| Coloring | 0.1 | 0.1 | 0.1 | 0.1 | 0.1 | 0.1 |
| TOTAL | 100 | 100 | 100 | 100 | 100 | 100 |
| Components and Relational Ratios | | | | | | |
| Ratio Gelatin to Plasticizer | 0.44 | 0.64 | 0.80 | 1.11 | 1.33 | 1.83 |
| Ratio Gelatin to Polymer Modifier | 27.0 | 320.0 | 50.0 | 55.7 | 40.0 | 42.3 |
| Matrix Fill Formulation | | | | | | |
| Hydrophilic Vehicle | 21 | 27 | 31 | 38 | 47 | 55 |
| Sweeteners | 68.5 | 61.5 | 55 | 52.75 | 34 | 31.5 |
| Flavorings | 1 | 4.1 | 2.5 | 3.24 | 5 | 5.5 |
| Solvents | 3.9 | 2.9 | 9.9 | 2.65 | 12.9 | 6.9 |
| Coloring | 0.1 | 0.1 | 0.1 | 0.1 | 0.1 | 0.1 |
| Active Pharmaceutical Ingredient (API) | 5.5 | 4.2 | 2.1 | 3.75 | 1 | 1 |
| TOTAL | 100% | 100% | 100% | 100% | 100% | 100% |
| Components and Relational Ratios | | | | | | |
| Ratio API to remaining ingredients | 0.06 | 0.04 | 0.02 | 0.04 | 0.01 | 0.01 |
| Ratio API to Hydrophilic Vehicle | 0.26 | 0.16 | 0.07 | 0.1 | 0.02 | 0.02 |

Example 16

Exemplary capsule shell and matrix compositions useful for producing Liquisoft capsules as described herein are shown in Table 18. Composition components are set forth by weight percentage of the total weight of the composition. Such compositions may be encapsulated using rotary die encapsulation as described herein.

TABLE 18

Exemplary Liquisoft Compositions

| | Weight Percentage (%) | | | | | |
|---|---|---|---|---|---|---|
| Component | EX 1 | EX 2 | EX 3 | EX 4 | EX 5 | EX 6 |
| Capsule Shell Formulation | | | | | | |
| Gelatin 150B | 14 | 18 | 20 | 22 | 27 | 31 |
| Gelatin 100B | 8 | 10 | 9 | 12 | 8 | 19 |

TABLE 18-continued

Exemplary Liquisoft Compositions

| Component | EX 1 | EX 2 | EX 3 | EX 4 | EX 5 | EX 6 |
|---|---|---|---|---|---|---|
| Gelatin Hydrolysate | 5 | 4 | 6 | 5 | 5 | 5 |
| Glycerol | 47 | 24 | 29 | 31 | 24.5 | 13.4 |
| Maltitol | | | 19 | 10 | | 14.5 |
| Xylitol | 14.5 | 6.5 | 4.8 | 3.5 | 5 | 2 |
| Citrate | 1 | 0.1 | 0.7 | — | — | 1.3 |
| Lactate | — | — | — | 0.7 | 1 | — |
| Sucralose | 0.5 | 0.5 | 0.2 | 0.5 | 0.5 | 0.1 |
| Solvent | 9.4 | 17.4 | 20.4 | 25.4 | 28.4 | 13.4 |
| Flavor | 0.5 | 0.5 | 0.5 | 0.5 | 0.5 | 0.5 |
| Coloring | 0.1 | 0.1 | 0.1 | 0.1 | 0.1 | 0.1 |
| TOTAL | 100% | 100% | 100% | 100% | 100% | 100% |
| Matrix Fill Formulation | | | | | | |
| Propylene Glycol | 2.5 | 5 | 6.5 | 7 | 9 | 6 |
| Polyethylene Glycol 400 | 18 | 21 | 24 | 30 | 37 | 48 |
| Polyvinylpyrrolidone K30 | 0.5 | 1 | 0.5 | 1 | 0.5 | 1 |
| Citric Acid | 0.33 | 1.37 | 0.83 | 1.08 | 1.67 | 2.75 |
| Lactic Acid | 0.33 | 1.37 | 0.83 | 1.08 | 1.67 | 2.75 |
| Sodium Citrate | 0.33 | 1.37 | 0.83 | 1.08 | 1.67 | — |
| Maltitol | 67 | 58 | 51.5 | 48.5 | 29.5 | 28.75 |
| Sucralose | 1 | 1 | 0.5 | 0.5 | 1.5 | 1.25 |
| Mannitol | 0.5 | — | — | — | 3 | — |
| Talin | — | 2.5 | — | 3.75 | — | 1.5 |
| MagnaSweet ® | — | — | 3 | — | — | — |
| Solvent | 3.9 | 2.9 | 9.9 | 2.65 | 12.9 | 6.9 |
| Coloring | 0.1 | 0.1 | 0.1 | 0.1 | 0.1 | 0.1 |
| Active Pharmaceutical Ingredient (API) | 5.5 | 4.2 | 2.1 | 3.75 | 1 | 1 |
| TOTAL | 100% | 100% | 100% | 100% | 100% | 100% |

Example 17

Exemplary capsule shell and matrix compositions useful for producing Liquisoft capsules as described herein are shown in Tables 19-21. Composition components are set forth by the quantity and weight percentage of the total weight of the composition.

TABLE 19

Exemplary Liquisoft Shell Composition

| Component | Quantity (kg) | Weight Percentage (%) |
|---|---|---|
| Gelatin, 150 Bloom Limed Bone, NF | 79.5 | 19.3 |
| Gelatin, 100 Bloom Limed Bone, NF | 34.2 | 8.30 |
| Hydrolyzed Collagen Peptan B 5000 HD | 20.0 | 4.85 |
| Glycerin, USP | 98.7 | 23.95 |
| Citric Acid Anhydrous, USP | 2.16 | 0.52 |
| Lycasin 80/55 | 69.0 | 16.75 |
| Xylisorb 300, USP | 10.8 | 2.62 |
| Orange Flavor PB72 | 2.16 | 0.52 |
| FD&C Yellow #6, Granular | 0.08 | 0.02 |
| FD&C Red #40 | 0.02 | 0.0049 |
| Sucralose, USP | 0.84 | 0.20 |
| Purified Water | 94.6 | 22.96 |
| TOTAL | 412.06 | 100.0% |

TABLE 20

Exemplary Liquisoft Fill Composition

| Component | Quantity (mg) | Weight Percentage (%) |
|---|---|---|
| Dextromethorphan HBr, USP | 15.8* | 1.6 |
| L-Menthol Crystals, USP | 0.9 | 0.1 |
| PEG 400, USP | 195.0 | 19.5 |
| Propylene Glycol, USP | 80.0 | 8.0 |
| Polyvinylpyrrolidone K30 | 12.0 | 1.2 |
| Lactic Acid, USP | 10.0 | 1.0 |
| Citric Acid | 10.0 | 1.0 |
| γ-Cyclodextrin | 22.0 | 2.2 |
| Sucralose, USP | 5.9 | 0.6 |
| Acesulfame potassium | 6.0 | 0.6 |
| Lycasin 80/55 | 551.4 | 55.1 |
| Orange Flavor PB72 | 16.0 | 1.6 |
| Purified Water | 75.0 | 7.5 |
| TOTAL | 1000.0 | 100.0% |

*Dextromethorphan HBr is corrected for its impurity (impurity factor of 0.951).

TABLE 21

Exemplary Liquisoft Fill Composition

| Component | Quantity (mg) | Weight Percentage (%) |
|---|---|---|
| Dextromethorphan HBr, USP | 15.8* | 1.6 |
| L-Menthol Crystals, USP | 2.5 | 0.3 |
| PEG 400, USP | 195.0 | 19.5 |
| Propylene Glycol, USP | 80.0 | 8.0 |
| Polyvinylpyrrolidone K30 | 12.0 | 1.2 |
| Lactic Acid, USP | 10.0 | 1.0 |
| Citric Acid | 10.0 | 1.0 |
| γ-Cyclodextrin | 22.0 | 2.2 |
| Sucralose, USP | 5.9 | 0.6 |
| Acesulfame potassium | 6.0 | 0.6 |
| Lycasin 80/55 | 549.8 | 55 |
| Orange Flavor PB72 | 16 | 16 |
| Purified Water | 75 | 7.5 |
| TOTAL | 1000.0 | 100.0% |

*Dextromethorphan HBr is corrected for its impurity (impurity factor of 0.951).

Example 18

Exemplary capsule shell and matrix compositions useful for producing Liquisoft capsules as described herein are shown in Tables 22-23. Composition components are set forth by weight percentage of the total weight of the composition. Such compositions may be encapsulated using rotary die encapsulation as described herein.

TABLE 22

Exemplary Liquisoft Shell Composition

| Component | Quantity (kg) | Weight Percentage (%) | Mass per capsule (mg) |
|---|---|---|---|
| Gelatin, 150 Bloom Limed Bone | 79.50 | 19.9 | 111.2 |
| Gelatin, 100 Bloom Limed Bone | 34.20 | 8.6 | 47.8 |
| Hydrolyzed Collagen Peptan B 5000 HD | 20.00 | 5.0 | 28.0 |
| Lycasin 80/55 | 67.60 | 16.9 | 94.6 |
| Glycerin, USP | 98.70 | 24.7 | 138.0 |
| Purified Water (I)* | 82.00 | 20.5 | 114.7 |
| FD&C Yellow #6, Granular | 0.08 | 0 | 0.1 |
| FD&C Red #40 | 0.02 | 0 | 0.0 |
| Purified Water (II)** | 1.00 | 0.3 | 1.4 |
| Orange Flavor PB72 | 3.50 | 0.9 | 4.9 |

TABLE 22-continued

Exemplary Liquisoft Shell Composition

| Component | Quantity (kg) | Weight Percentage (%) | Mass per capsule (mg) |
|---|---|---|---|
| Xylisorb 300, USP | 10.00 | 2.5 | 15.1 |
| Citric Acid Anhydrous, USP | 2.10 | 0.5 | 3.0 |
| Sucralose, USP | 0.84 | 0.2 | 1.2 |
| TOTAL | 399.54 | 100.0% | 560.0 |

TABLE 23

Exemplary Liquisoft Fill Compositions

| Component | Quantity (mg) | Weight Percentage (%) | Quantity (mg) | Weight Percentage (%) |
|---|---|---|---|---|
| Dextromethorphan HBR | 10.52 | 1.1 | 10.52 | 1.1 |
| L-Menthol | 0.65 | 0.1 | 2.50 | 0.3 |
| PEG 400 | 210.00 | 21.0 | 210.00 | 21.0 |
| Propylene Glycol | 80.00 | 8.0 | 80.00 | 8.0 |
| Lactic Acid | 10.00 | 1.0 | 10.00 | 1.0 |
| Purified Water | 55.00 | 5.5 | 55.00 | 5.5 |
| Citric Acid | 10.00 | 1.0 | 10.00 | 1.0 |
| Polyvinylpyrrolidone K30 | 12.00 | 1.2 | 12.00 | 1.2 |
| Sucralose | 5.90 | 0.6 | 5.90 | 0.6 |
| Acesulfame potassium | 6.00 | 0.6 | 6.00 | 0.6 |
| Lycasin 80/55 | 579.93 | 58.0 | 578.08 | 57.8 |
| Orange Flavor | 20.00 | 2.0 | 20.00 | 2.0 |
| TOTAL | 1000.0 | 100.0% | 1000.0 | 100.0% |

Example 19

Exemplary capsule shell and matrix compositions useful for producing Liquisoft capsules as described herein are shown in Tables 24-25. Composition components are set forth by weight percentage of the total weight of the composition. Such compositions may be encapsulated using rotary die encapsulation as described herein.

TABLE 24

Exemplary Liquisoft Shell Composition

| Component | Quantity (kg) | Weight Percentage (%) |
|---|---|---|
| Gelatin, LB, 100 Bloom | 114.0 | 27.76 |
| Hydrolyzed Collagen Peptan B 5000 HD | 20.0 | 4.87 |
| Lycasin 80/55 | 69.0 | 16.80 |
| Glycerin, USP | 88.0 | 21.43 |
| Propylene Glycol, USP | 4.0 | 0.97 |
| Purified Water (I) | 89.0 | 21.67 |
| FD&C Yellow #6, Granular | 0.02616 | 0.01 |
| FD&C Blue #1 | 0.01132 | 0.003 |
| Purified Water (II) | 1.0 | 0.24 |
| Peppermint Oil | 0.396 | 0.10 |
| Xylisorb 300, USP | 10.2 | 2.48 |
| Citric Acid Anhydrous, USP | 2.16 | 0.53 |
| Sucralose, USP | 0.84 | 0.20 |
| Purified Water (III) | 12.0 | 2.92 |
| TOTAL | 410.63 | 100.0% |

TABLE 25

Exemplary Liquisoft Fill Composition

| Component | Quantity (kg) | Weight Percentage (%) |
|---|---|---|
| Sorbitol Special | 12.03 | 40.1 |
| L-Menthol Flakes Pharma | 0.057 | 0.2 |
| Glycerin, USP | 12.45 | 41.5 |
| Propylene Glycol, USP | 0.60 | 2.0 |
| Polysorbate 20, NF | 0.60 | 2.0 |
| Purified Water | 3.0 | 10.0 |
| Citric Acid | 0.075 | 0.3 |
| Polyvinylpyrrolidone K30 | 0.90 | 3.0 |
| Sucralose, USP | 0.15 | 0.5 |
| Thymol, Crystal NF | 0.0012 | 0 |
| Eucalyptol | 0.0276 | 0. |
| Peppermint Oil | 0.090 | 0.3 |
| Methyl salicylate | 0.018 | 0.1 |
| TOTAL | 29.9988 | 100.0% |

Example 20

Exemplary capsule shell and matrix compositions useful for producing Liquisoft capsules as described herein are shown in Tables 26-27. Composition components are set forth by weight percentage of the total weight of the composition. Such compositions may be encapsulated using rotary die encapsulation as described herein.

TABLE 26

Exemplary Liquisoft Shell Composition

| Component | Quantity (kg) | Weight Percentage (%) |
|---|---|---|
| Gelatin, LB, 150 Bloom | 22 | 22.00 |
| Gelatin, LB, 100 Bloom | 10 | 10.00 |
| Maltitol Syrup | 17.25 | 17.25 |
| Glycerin 99.7% | 19.7 | 19.70 |
| Titanium dioxide | 2.1 | 2.10 |
| Purified Water I | 18.2 | 18.20 |
| Gelatin Hydrolysate | 5 | 5.00 |
| Xylisorb 300 | 2.55 | 2.55 |
| Citric Acid | 0.54 | 0.54 |
| Sucralose | 0.21 | 0.21 |
| Purified Water II | 3.15 | 3.15 |
| Peppermint Oil | 0.3 | 0.30 |
| TOTAL* | 101 | 101.0 |

Components in the indented rows are mixed separately and then combined with the mixture of the other components.
*Shell contains 1% excess water to compensate vapor loss during vacuum deaeration.

TABLE 27

Exemplary Liquisoft Fill Composition

| Component | Quantity (kg) | Weight Percentage (%) |
|---|---|---|
| Gelatin 70 Bloom LB | 75.0 | 7.5 |
| Glycerin | 185.0 | 18.5 |
| Purified water I | 107.0 | 10.7 |
| Gelatin hydrolysate | 90.0 | 9.0 |
| Maltitol Syrup | 370.0 | 37.0 |
| Glycine | 50.0 | 5.0 |
| Purified water II | 30.0 | 3.0 |
| Xylisorb 300 | 30.0 | 3.0 |
| Menthol (crystal) | 0.4 | 0.04 |
| Peppermint oil | 0.4 | 0.04 |
| PEG-400 | 10.0 | 1.0 |

TABLE 27-continued

Exemplary Liquisoft Fill Composition

| Component | Quantity (kg) | Weight Percentage (%) |
|---|---|---|
| Sucralose | 2.0 | 0.2 |
| Purified water III | 30.2 | 3.0 |
| Nicotine Polacrilex (~20%)* | 20.0 | 2.0 |
| TOTAL | 1000.0 | 100.0% |

Components in the indented rows are mixed separately and then combined with the mixture of the other components.
*The amount of active is variable according to the certificate of analysis (COA) of the Nicotine Polacrilex lot. The difference is accounted for by the adjusting the glycine amount.

Example 21

Exemplary capsule shell and matrix compositions useful for producing Liquisoft capsules as described herein are shown in Tables 28-29. Composition components are set forth by weight percentage of the total weight of the composition. Such compositions may be encapsulated using rotary die encapsulation as described herein.

TABLE 28

Exemplary Liquisoft Shell Composition

| Component<br>Gel Component | Quantity (kg)<br>Mass (kg) | Weight Percentage (%)<br>% weight |
|---|---|---|
| Gelatin, LB, 100 Bloom | 52.64 | 12.82 |
| Gelatin, LB, 150 Bloom | 77.20 | 18.79 |
| Glycerin | 91.84 | 22.36 |
| TiO2 Mass | 6.00 | 1.46 |
| Gelatin hydrolysate | 9.72 | 2.37 |
| Maltitol syrup | 57.48 | 13.99 |
| Purified Water I | 86.60 | 21.08 |
| FD&C Red #40 | 0.02 | 0.00 |
| D&C Red #33 | 0.02 | 0.01 |
| Purified Water II* | 2.00 | 0.49 |
| Cherry Flavor** | 2.00 | 0.49 |
| Xylisorb 300, USP | 10.20 | 2.48 |
| Citric acid anhydrous, USP | 2.20 | 0.54 |
| Sucralose, USP | 0.84 | 0.2 |
| Purified Water III*** | 12.00 | 2.92% |
| TOTAL**** | 410.76 | 100.0% |

*Purified Water II serves to dissolve colorants.
**Cherry Flavor is added to the gel on the day of encapsulation.
***Purified Water III serves to dissolve sweeteners. The sweetener solution is to be added to the gel on the day of encapsulation.
****There is 2% extra water to compensate for vapor loss during vacuum deaeration. Components in the indented rows are mixed separately and then combined with the mixture of the other components.

TABLE 29

Exemplary Liquisoft Fill Composition

| Component | Quantity (kg) | Weight Percentage (%) |
|---|---|---|
| Glycerin | 0.630 | 1.78 |
| Gelatin hydrolysate | 0.630 | 1.78 |
| Gelatin, 70B LB | 0.630 | 1.78 |
| Sorbitol Special | 9.450 | 26.72 |
| Xylisorb 300 | 0.950 | 2.69 |
| Propylene glycol 1 | 2.050 | 5.80 |
| PEG-400 | 0.320 | 0.90 |
| Sucralose | 0.063 | 0.18 |
| Purified Water 1* | 3.670 | 10.38 |
| FD&C Red #40 | 0.002 | 0.00 |
| FD&C Red #33 | 0.002 | 0.01 |
| Purified Water 2 | 0.079 | 0.22 |
| Menthol (crystal) | 0.016 | 0.04 |
| Peppermint oil | 0.016 | 0.04 |

TABLE 29-continued

Exemplary Liquisoft Fill Composition

| Component | Quantity (kg) | Weight Percentage (%) |
|---|---|---|
| Propylene glycol 2 | 0.320 | 0.90 |
| Simethicone | 0.001 | 0 |
| Bismuth Subsalicylate | 16.540 | 46.77 |
| TOTAL** | 35.37 | 100.0% |

*There is 1% extra water to compensate for vapor loss during vacuum deaeration.
**Theoretical total batch weight is 35.02 kg after excluding 0.35 kg additional water. Nitrogen blanketing is maintained throughout the compounding process and storage period. Components in the indented rows are mixed separately and then combined with the mixture of the other components.

What is claimed is:

1. An oral pharmaceutical composition suitable for chewing, sucking, or buccal dissolution comprising a soft shell encapsulating a liquid matrix,
    the shell comprising:
        (a) about 20% gelatin, 150 Bloom;
        (b) about 9% gelatin, 100 Bloom;
        (c) about 5% hydrolyzed collagen;
        (d) about 17% lycasin;
        (e) about 25% glycerin;
        (f) about 0.5% citric acid;
        (g) about 2.5% about xylitol,
        (h) about 0.2% sucralose; and
        (i) about 21% water; and
    the matrix comprising:
        (j) about 21% polyethylene glycol 500,
        (k) about 8% propylene glycol;
        (l) about 1% polyvinylpyrrolidone K30;
        (m) about 58% lycasin;
        (n) about 1% citric acid;
        (o) about 1% lactic acid;
        (p) about 0.6% sucralose,
        (q) about 0.6% acesulfame potassium;
        (r) about 5% water;
        (s) about 1% dextromethorphan hydrobromide; and
        (t) about 0.1% menthol.

2. An oral pharmaceutical composition suitable for chewing, sucking, or buccal dissolution comprising a soft shell encapsulating a liquid matrix,
    the shell comprising:
        (a) about 27% gelatin, 100 Bloom;
        (b) about 5% hydrolyzed collagen;
        (c) about 17% lycasin;
        (e) about 21% glycerin;
        (f) about 1% propylene glycol;
        (g) about 0.5% citric acid;
        (h) about 2.5% xylitol;
        (i) about 0.8% sucralose;
        (j) about 0.1% peppermint oil;
        (k) about 24% water; and
    the matrix comprising:
        (l) about 42% glycerin;
        (m) about 2% propylene glycol;
        (n) about 3% polyvinylpyrrolidone K30;
        (o) about 40% sorbitol;
        (p) about 0.3% citric acid;
        (q) about 0.5% sucralose;
        (r) about 0.1% eucalyptol;
        (s) about 0.3% peppermint oil;
        (t) about 10% water;
        (u) about 0.004% thymol; and
        (v) about 0.2% menthol.

3. An oral pharmaceutical composition suitable for chewing, sucking, or buccal dissolution comprising a soft shell encapsulating a liquid matrix:
the shell comprising:
(a) about 22% gelatin, 150 Bloom;
(b) about 10% gelatin, 100 Bloom;
(c) about 5% gelatin hydrolysate;
(d) about 20% glycerin;
(e) about 17% maltitol;
(f) about 0.5% citric acid;
(g) about 2.6% xylitol;
(h) about 0.2% sucralose;
(i) about 0.3% peppermint oil; and
(j) about 21% water; and
the matrix comprising:
(k) about 1% polyethylene glycol 400;
(l) about 19% glycerin;
(m) about 3% xylitol;
(n) about 37% maltitol;
(o) about 5% glycine;
(p) about 0.2% sucralose;
(q) about 0.04% menthol;
(r) about 0.04% peppermint oil;
(s) about 17% water; and
(t) about 2% nicotine polacrilex.

4. An oral pharmaceutical composition suitable for chewing, sucking, or buccal dissolution comprising a soft shell encapsulating a liquid matrix:
the shell comprising:
(a) about 19% gelatin, 150 Bloom;
(b) about 13% gelatin, 100 Bloom;
(c) about 2% gelatin hydrolysate;
(d) about 22% glycerin;
(e) about 14% maltitol;
(f) about 0.5% citric acid;
(g) about 2.5% xylitol;
(h) about 0.2% sucralose; and
(i) about 29% water; and
the matrix comprising:
(j) about 1% polyethylene glycol 400;
(k) about 2% glycerin;
(l) about 6% propylene glycol;
(m) about 27% sorbitol;
(n) about 3% xylitol;
(o) about 0.2% sucralose;
(p) about 0.04% menthol;
(q) about 0.04% peppermint oil;
(r) about 11% water; and
(s) about 47% bismuth subsalicylate.

5. A kit for dispensing the oral pharmaceutical composition of claim 1, the kit comprising:
(a) at least one oral pharmaceutical composition;
(b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally
(c) at least one daily regimen for the oral pharmaceutical composition; and
(d) an insert comprising instructions or prescribing information for the oral pharmaceutical composition.

6. A pharmaceutical combination comprising the oral pharmaceutical composition of claim 1 and one or more additional therapeutic compounds selected from NSAIDS, diphenhydramine, or codeine.

7. A method for treating, retarding the progression of, prophylaxis of, delaying the onset of, ameliorating, reducing the symptoms of inflammation, cough, cold, chest congestion, nasal congestion, sinusitis, throat or bronchial irritation, flu, fever, or pain comprising administering to a subject in need thereof the oral pharmaceutical composition of claim 1.

8. A kit for dispensing the oral pharmaceutical composition of claim 2, the kit comprising:
(a) at least one oral pharmaceutical composition;
(b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally
(c) at least one daily regimen for the oral pharmaceutical composition; and
(d) an insert comprising instructions or prescribing information for the oral pharmaceutical composition.

9. A pharmaceutical combination comprising the oral pharmaceutical composition of claim 2 and one or more additional therapeutic compounds selected from chlorhexidine or ethanol.

10. A method for treating, retarding the progression of, prophylaxis of, delaying the onset of, ameliorating, reducing the symptoms of, or promoting health, including but not limited to of one or more of dry mouth, halitosis, stained teeth, oral pain, loss of enamel, refreshing breath, inhibiting onset of breath malodor, or freshening the oral cavity comprising administering to a subject in need thereof the oral pharmaceutical composition of claim 2.

11. A kit for dispensing the oral pharmaceutical composition of claim 3, the kit comprising:
(a) at least one oral pharmaceutical composition;
(b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally
(c) at least one daily regimen for the oral pharmaceutical composition; and
(d) an insert comprising instructions or prescribing information for the oral pharmaceutical composition.

12. A pharmaceutical combination comprising the oral pharmaceutical composition of claim 3 and one or more additional therapeutic compounds selected from bupropion or varenicline.

13. A method for treating, retarding the progression of, prophylaxis of, delaying the onset of, ameliorating, or reducing the symptoms of, or promoting health, including but not limited to cessation of urge to smoke, satiating nicotine desire, nicotine-replacement therapy, or smoking cessation therapy comprising administering to a subject in need thereof the oral pharmaceutical composition of claim 3.

14. A kit for dispensing the oral pharmaceutical composition of claim 4, the kit comprising:
(a) at least one oral pharmaceutical composition;
(b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally
(c) at least one daily regimen for the oral pharmaceutical composition; and
(d) an insert comprising instructions or prescribing information for the oral pharmaceutical composition.

15. A pharmaceutical combination comprising the oral pharmaceutical composition of claim 4 and one or more additional therapeutic compounds selected from cimetidine, ranitidine, famotidine, ondansetron, omeprazole, lansoprazole, rabeprazole, esomeprazole, pantoprazole, calcium supplements, calcium hydroxide, alluminum hydroxide, magnesium hydroxide, or combinations thereof.

16. A method for treating, retarding the progression of, prophylaxis of, delaying the onset of, ameliorating, or reducing the symptoms of, or promoting health, including but not limited to of one or more of inflammation of the gastrointestinal tract, neoplasia, hyperthyroidism, hypercalcemia, hyperparathyroidism, parathyroid carcinoma, indigestion, heartburn, nausea, flatulence, bloating, acid reflux, irritable bowels, constipation, diarrhea, comprising administering to a subject in need thereof comprising administering to a subject in need thereof the oral pharmaceutical composition of claim 4.

* * * * *